US010525150B2

(12) United States Patent
Yang et al.

(10) Patent No.: US 10,525,150 B2
(45) Date of Patent: Jan. 7, 2020

(54) TARGETED CONTRAST AGENTS AND METHODS FOR TARGETING CONTRAST AGENTS

(71) Applicant: Georgia State University Research Foundation, Inc., Atlanta, GA (US)

(72) Inventors: Jenny J. Yang, Atlanta, GA (US); Zhi-Ren Liu, Atlanta, GA (US)

(73) Assignee: Georgia State University Research Foundation, Inc., Atlanta, GA (US)

( * ) Notice: Subject to any disclaimer, the term of this patent is extended or adjusted under 35 U.S.C. 154(b) by 0 days.

(21) Appl. No.: 15/155,958

(22) Filed: May 16, 2016

(65) Prior Publication Data

US 2016/0250356 A1 Sep. 1, 2016

Related U.S. Application Data

(63) Continuation of application No. 11/530,398, filed on Sep. 8, 2006, now Pat. No. 9,339,559, and a continuation-in-part of application No. 11/457,370, filed on Jul. 13, 2006, now Pat. No. 8,173,105.

(60) Provisional application No. 60/715,493, filed on Sep. 9, 2005, provisional application No. 60/699,409, filed on Jul. 13, 2005.

(51) Int. Cl.
*A61K 49/00* (2006.01)
*A61K 38/02* (2006.01)
*A61K 49/14* (2006.01)
*A61K 49/08* (2006.01)

(52) U.S. Cl.
CPC .............. *A61K 49/14* (2013.01); *A61K 38/02* (2013.01); *A61K 49/0002* (2013.01); *A61K 49/0047* (2013.01); *A61K 49/085* (2013.01)

(58) Field of Classification Search
None
See application file for complete search history.

(56) References Cited

U.S. PATENT DOCUMENTS

| | | | |
|---|---|---|---|
| 4,508,625 A | 4/1985 | Graham |
| 5,679,548 A | 10/1997 | Barbas et al. |
| 5,690,903 A | 11/1997 | Hainfelt et al. |
| 5,922,302 A | 7/1999 | Goldenberg et al. |
| 6,197,258 B1 | 3/2001 | Thompson |
| 6,197,928 B1 | 3/2001 | Tsein et al. |
| 6,207,133 B1 | 3/2001 | Reszka |
| 6,469,154 B1 | 10/2002 | Tsein et al. |
| 6,709,646 B2 | 3/2004 | Lauffer et al. |
| 2002/0015038 A1 | 2/2002 | Patel |
| 2002/0123113 A1 | 9/2002 | Tsien et al. |
| 2002/0136692 A1 | 9/2002 | Haroon et al. |
| 2002/0160473 A1 | 10/2002 | Lukyanov |
| 2003/0149254 A1 | 8/2003 | Anderson et al. |
| 2003/0180222 A1 | 9/2003 | Zhang et al. |
| 2003/0228622 A1 | 12/2003 | Imperiali et al. |
| 2004/0115132 A1 | 6/2004 | Young et al. |
| 2004/0171107 A1 | 9/2004 | Nelson et al. |
| 2004/0208827 A1 | 10/2004 | McMurry et al. |
| 2005/0221289 A1 | 10/2005 | Green et al. |
| 2006/0029942 A1 | 2/2006 | Yang |
| 2006/0030029 A1 | 2/2006 | Yang |
| 2006/0031020 A1 | 2/2006 | Yang |
| 2006/0035289 A1 | 2/2006 | Matsudaira et al. |

FOREIGN PATENT DOCUMENTS

| | | | |
|---|---|---|---|
| EP | 1238982 A1 | 9/2002 | |
| WO | 2001030398 A2 | 3/2001 | |
| WO | 2003014157 A2 | 2/2003 | |
| WO | 2003057829 A2 | 7/2003 | |
| WO | 2005016387 A2 | 2/2005 | |
| WO | 2005097208 A2 | 10/2005 | |
| WO | 2006080022 A3 | 8/2006 | |
| WO | WO-2007009058 A2 * | 1/2007 | ......... A61K 49/0002 |

OTHER PUBLICATIONS

Heylin, M., et al., "Chemistry Grads Post Gains in 2005", ACS News, 2006, pp. 43-52 (Year: 2006).*
Wilkins, A., et al. "Metal-binding studies fora de novo designed calcium-binding protein", Protein Engineering, 2002, pp. 571-574 (Year: 2002).*
Supplementary European Search Report for EP 09 75 5461 dated Sep. 16, 2014.
Patonay, et al., Near-Infrared Fluorogenic Labels: New Approach to an Old Problem, Analytical Chem 63:6, 1991, pp. 321-327.
Romoser, et al., Detection of Living Cells of Ca2+-dependent Changes in the Fluorescence Emission of an Indicator Composed of Two Green Fluorescent Protein Variants Linked by a Calmodulin-binding Sequence, Journal of Bio Chem 272:20, 1997, pp. 13270-13274.
Supplementary European Search Report for EP05783374 dated Aug. 25, 2009.
Smith, et al., entry for "Quaternary Structure," Oxford Dictionary of Biochemistry and Molecular Biology, OUP, New York: 1997, pp. 551.
Response to Election/Restriction for U.S. Appl. No. 10/914,769, filed Sep. 8, 2006.
Amendment/Req. Reconsideration After Non-Final Rejection for U.S. Appl. No. 10/914,769, filed Feb. 22, 2017.
Amendment Submitted/Entered with Filing of a CPA/RCE for U.S. Appl. No. 10/914,769, filed Nov. 19, 2007.
Amendment/Req. Reconsideration After Non-Final Rejection for U.S. Appl. No. 10/914,769, filed Aug. 21, 2008.
Amendment/Req. Reconsideration After Non-Final Rejection for U.S. Appl. No. 10/914,769, filed Oct. 2, 2009.

(Continued)

*Primary Examiner* — Michael G. Hartley
*Assistant Examiner* — Lance W Rider
(74) *Attorney, Agent, or Firm* — Thomas|Horstemeyer, LLP

(57) ABSTRACT

A contrast agent having a contrast protein have contrast properties and at least one targeting moiety, wherein the at least one targeting moiety is operatively linked to or incorporated within the contrast protein. Methods for targeting contrast agents and for preparing such agents are included.

8 Claims, 7 Drawing Sheets
Specification includes a Sequence Listing.

(56) References Cited

OTHER PUBLICATIONS

Response After Final Action for U.S. Appl. No. 10/914,769, filed Mar. 26, 2010.
Amendment/Req. Reconsideration After Non-Final Rejection for U.S. Appl. No. 10/914,769, filed Oct. 28, 2010.
Appeal Brief for U.S. Appl. No. 10/914,769, filed Mar. 22, 2011.
Reply Brief for U.S. Appl. No. 10/914,769, filed Jul. 18, 2011.
Declaration of Jun Yin under 37 CFR 1.132 for U.S. Appl. No. 10/914,769, filed Mar. 24, 2014.
Response to Decision on Appeal and RCE for U.S. Appl. No. 10/914,769, filed Mar. 24, 2014.
Declaration of Jun Yin under 37 CFR 1.132 for U.S. Appl. No. 10/914,769, filed Feb. 4, 2015.
Amendment/Req. Reconsideration After Non-Final Rejection for U.S. Appl. No. 10/914,769, filed Feb. 4, 2015.
Response to Restriction/Election for U.S. Appl. No. 11/457,370, filed May 20, 2010.
Amendment/Req. Reconsideration After Non-Final Rejection for U.S. Appl. No. 11/457,370, filed Oct. 29, 2010.
Response After Final Action for U.S. Appl. No. 11/457,370, filed Mar. 9, 2011.
Amendment/Req. Reconsideration After Non-Final Rejection for U.S. Appl. No. 11/457,370, filed Jun. 22, 2011.
International Preliminary Report on Patentability for PCT/US2009/039276 dated Oct. 5, 2010.
Response to Election/Restriction for U.S. Appl. No. 12/935,413, filed Mar. 30, 2012.
Amendment/Req. Reconsideration After Non-Final Rejection for U.S. Appl. No. 12/935,413, filed Nov. 2, 2012.
Response After Final Action for U.S. Appl. No. 12/935,413, filed Jun. 18, 2013.
Declaration of Dr. Jun Yin under 37 CFR 1.132 for U.S. Appl. No. 12/935,413, filed Jan. 22, 2015.
Amendment/Req. Reconsideration After Non-Final Rejection for U.S. Appl. No. 12/935,413, filed Jan. 22, 2015.
Declaration of Dr. Jun Yin under 37 CFR 1.132 for U.S. Appl. No. 12/935,413, filed May 13, 2015.
Appeal Brief for U.S. Appl. No. 12/935,413, filed May 13, 2015.
Reply Brief for for U.S. Appl. No. 12/935,413, filed Nov. 23, 2015.
Response to Election/Restriction for U.S. Appl. No. 14/405,623, filed Nov. 21, 2016.
International Search Report and Written Opinion for PCT/US2006/035221 dated Nov. 28, 2007.
Cohen, et al., "Ferritin as an Endogenous MRI Reporter for Non-invasive Imaging of Gene Expression in C6 Glioma Tumors," Neoplasia 7:2, Feb. 2005, pp. 109-117.
Anton, et al., "Biotinylation of a Bombesin/Gastrin-Releasing Peptide Analogue for Use as a Receptor Probe," Peptides 12, 1991, pp. 375-381.
Ye, et al., "Metal binding affinity and structural properties of an isolated EF-loop in a scaffold protein," Protein Engineering 14:12, 2001, pp. 1001-1013.
Heylin, "Chemistry Grads Post Gains in 2005," ACS News, Jul. 24, 2006, pp. 43-52.
Yang, et al., "Rational Design of a Calcium-Binding Protein," JACS 125, 2003, pp. 6165-6171
Lewit-Bentley, et al., "EF-hand calcium-binding proteins," Cur. Opinion Struct. Bio., 2000, pp. 637-643.
Birchmeier, et al., "Comparison of Human Hemoglobin a Carrying Glutathione as a Mixed Disulfide with the Naturally Occuring Human Hemoglobin A," Biochemistry 12:19, 1973, pp. 3667-3671.
Achilefu, et al., "Synthesis, In Vitro Receptor Binding, And In Vivo Evaluation of Fluorescein and Carbocyanine Peptide-Based Optical Contrast Agents," J. Med. Chem 45:10, 2002, pp. 2003-2015.
Gupta, et al., Targeted Contrast Agents in MR Imaging, Magnetic Resonance Imaging Clinics of North America 4:1, 1996, pp. 171-184.
Zhang H, et al., Synthesis and Evaluation of Bombesin Derivatives on the Basis of Pan-Bombesin Peptides Labeled with Indium-III, Lutetium-177, and Yttrium-90 for Targeting Bombesin Receptor-Expressing Tumors, Cancer Research (Sep. 15, 2004), vol. 64, No. 18, p. 6707-6715.
Japanese Office Action for Application No. 2008-530007 dated Jan. 24, 2012.
Canadian Search Report for Application No. 2,621,763 dated Jun. 25, 2014.
Canadian Office Action for Application No. 2,621,763 dated May 21, 2013.
Supplemental European Search Report for Application No. EP 06814414 dated Mar. 10, 2011.
European Office Action for Application No. 06814414.6 dated Jul. 25, 2013.
Canadian Office Action for Application No. 2,621,763 dated Nov. 9, 2015.
Japanese Office Action for Application No. 2008-530007 dated Oct. 2, 2012.
Elbanowski, et al., Fluorescence of Lanthanide(III) Complexes in Aqueous Solutions: The Influence of pH and Solution Composition. Monatshfte fur Chemie 116, 1985, pp. 901-911.
Johnson, et al., Structural Changes Required for Activation of Protein C Are Induced by Ca2+ Binding to a High Affinity Site That Does Not Contain y-Carboxyglutamic Acid, Journal of Bio Chem 258:9, May 10, 1963, pp. 5554-5560.
Lewis, et al., Fluorescence binding assay for a small peptide based on a GFP fusion protein, Analytica Chimica Acta 397, 1999, pp. 279-286.
Schlyer, et al., Time-Resolved Room Temperature Protein Phosphorescence: Nonexponential Decay from Single Emitting Tryptophans, Biophysical Journal 67, Sep. 1994, pp. 1192-1202.
Shelling, et al., Proton Nuclear Magnetic Resonance Studies of the Interaction of the Lanthanide Ions Ytterbium and Lutetium with Apo- and Calcium-Saturated Porcine Intestinal Calcium Binding Protein, Biochemistry 24, 1985, 2332-2338.
Yang, et al., The molecular structure of green fluorescent protein, Nature Biotechnology 14, 1996, pp. 1246-1251.
Yang, et al., Obtaining site-specific calcium-binding affinities of calmodulin, Protein and Peptide Letters 10, 2003, pp. 331-345.
Kawasaki, et al., Classification and evolution of EF-hand proteins, BioMetals 11, 1998, pp. 277-295.
Miyawaki, et al., Fluorescent indicators for Ca2+ based on green fluorescent proteins and calmodulin, Nature 388, Aug. 28, 1997, pp. 882-887.
Wilkins, et al., Metal-binding studies for a de novo designed calcium-binding protein, Protein Engineering 15:7, 2002, pp. 571-574.
Supplementary European Search Report for Application No. EP 05783374 dated Aug. 25, 2009.
Richmond, et al., Engineered Metal Binding Sites on Green Fluorescence Protein, Biochem and Biophys Research Comm 268, 2000, 462-465.
Romoser, Valerie, et al., "Detection in Living Cells of Ca2+-dependent Changes in the Fluorescence Emission of an Indicator Composed of Two Green Fluorescent Protein Variants Linked by a Calmodulin-binding Sequence: zA New class of Fluorescent Indicators," Journal of Biological Chemistry, vol. 272, No. 20, 1997, pp. 13270-13274.
Nagai, et al., Circularly permuted green fluorescent proteins engineered to sense Ca2+, PNAS USA, National Academy of Science, Washington, D.C. 98:6, Mar. 13, 2001, pp. 3197-3202.
Hellinga, et al., Protein engineering and the development of generic biosensors, Trends in Biotechnology 16:4, 1998, pp. 183-189.
Mesecar et al. Orbital Steering in the Catalytic Power of Enzymes: Small Structural Changes with Large Catalytic consequences. Science 277 Jul. 11, 1997. pp. 202-206.
MacKenzie, et al., Bifunctional fusion proteins consisting of a single-chain antibody and an engineered lanthanide-binding protein. Immunotechnology 1, 1995, pp. 139-150.
Lee, et al., Isolated EF-loop III of calmodulin in a scaffold protein remains unpaired in solution using pulsed-field- gradient NMR spectroscopy, Biochimica et Biophysica Acta 1598, 2002, 80-87.
Prasher, et al., Primary structure of the Aequorea victoria green-fluorescent protein, Gene 111, 1992, 229-233.

(56) References Cited

OTHER PUBLICATIONS

Ye, et al., A grafting approach to obtain site-specific metal-binding properties of EF-hand proteins, Protein Engineering 16:6, 2003, pp. 429-434.

International Search Report and Written Opinion for PCT/US06/27327 dated Feb. 1, 2007.

Cohen, et al., Ferritin as an Endogenous MRI Reporter for Noninvasive Imaging of Gene Expression in C6 Glioma Tumors, Neoplasia 7:2, Feb. 2005, pp. 109-111.

Pessi, et al., A designed metal-binding protein with a novel fold, Nature 362, Mar. 1993, pp. 367-369.

Caravan,et al, Gadolinium-binding helix-turn-helix peptides: DNA-dependent MRI contrast agents, Chem. Commun 2003, pp. 2574-2575.

Roberts, et al., Chemistry for peptide and protein PEGylation, Adv Drug Delivery Reviews 54, 2002, 459-476.

Veronese, et al., PEGylation, successful approach to drug delivery, Drug Discovery Today 10:21, 2005, p. 1451-1458.

Bogdanov, et al., Long-circulating blood pool imaging agents, Adv Drug Delivery Reviews 16, 1995, 335-348.

Strijkers, et al., Relaxivity of lipsomal paramagnetic MRI contrast agents, Biology and Medicine 18, 2005, pp. 186-192.

Doble, et al., Optimization of the Relaxivity of MRI Contrast Agents: Effect of Poly(ethylene glycol) Chains on the Water-Exchange Rates of Gd IIi Complexes, J. Am Chem Soc 123, 2001, 10758-10759.

Mohs, et al, PEG-g-poly(GdDTPA-co-L-cystine): Effect of PEG Chain Length on in Vivo Contrast Enhancement in MRI, Biomacromolecules 2005:6, 2305-2311.

Ke, et al., Imagine Taxane-induced tumor apoptosis using PEGylated, 111I n-labeled annexin V, Journal of Nuclear Medicine 45, 2004, 108-115.

Canadian Search Report for Application No. 2,621,763 dated Mar. 7, 2018.

\* cited by examiner

Target sequences, Receptors, Cells

| Target Sequence | Receptor | Cell |
|---|---|---|
| Somatostatin | Somatostatin receptor subtypes sst1-5 | Neuroendocrine tumors, SCLC, MTC, tumors of the nervous system, lymphoma (non-Hodgkin's lymphoma, Hodgkin's disease) |
| VIP/PACAP | $VPAC_1$, $VPAC_2$, $PAC_1$ receptors | Various adenocarcinomas (stomach, colon, pancreas, lung, etc.) |
| CCK | $CCK_1$, $CCK_2$ receptors | MTC, SCLC, stromal ovarian cancer, astrocytoma |
| LHRH | LHRH receptors | Breast, prostate |
| α-MSH | MSH receptors | Melanoma |
| Bombesin/GRP | $BB_1$, $BB_2$, $BB_3$ and $BB_4$ receptors | SCLC, MTC, glioblastoma, colonic cancer, prostate cancer |
| Neurotensin | NTR1, NTR2, and NTR3 receptors | Ewing sarcoma, meningioma, MTC, astrocytoma, SCLC |
| Opioid | Opioid receptors | SCLC, neuroblastoma, breast cancer |
| Substance P | NK1 receptors | Glioblastoma, astrocytoma, MTC, breast, peri- and intratumoral blood vessels |
| GLP-1 | GLP-1 receptors | insulinomas |
| Oxytocin | Oxytocin receptors | Endometrium, breast cancer |
| Neuropeptide Y | NPY receptors subtype $Y_1$-$Y_6$ | Breast, brain cancer |
| EGFR | EGF receptor | Breast and many cancer cell types |
| Her-2 | Her-2 receptor | Cancer cells |

FIG. 2

| PC-3 | HCT-116 |
5 min
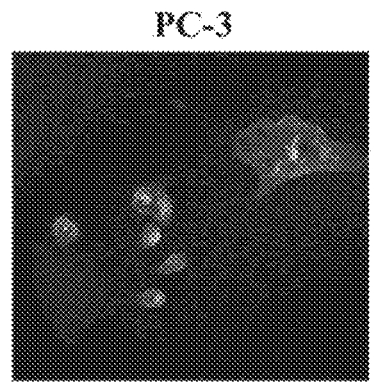 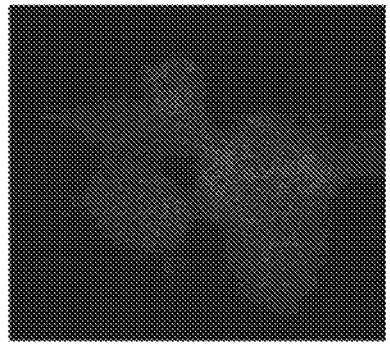
FIG. 4A  FIG. 4B
60 min
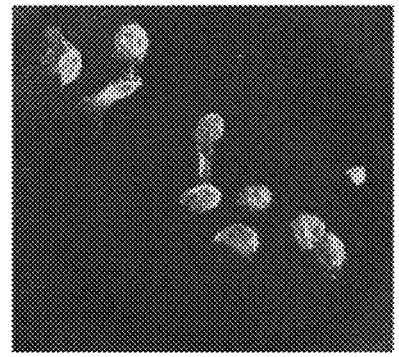 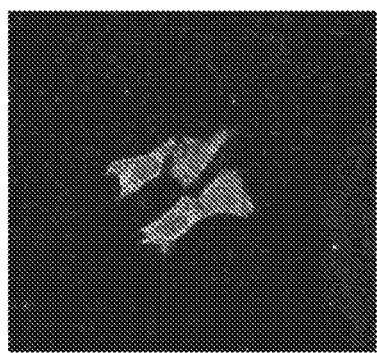
FIG. 4C  FIG. 4D
120 min
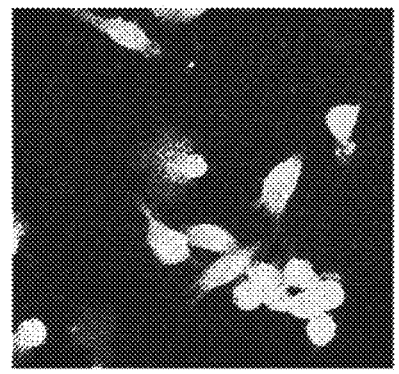 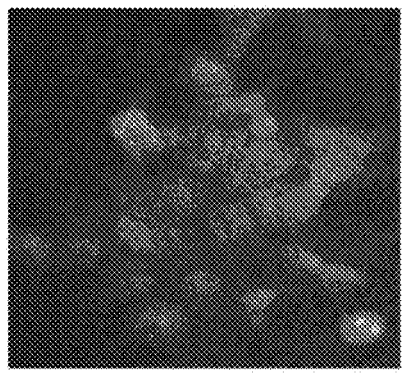
FIG. 4E  FIG. 4F GFP-7E15-Bom
PC-3 30mins
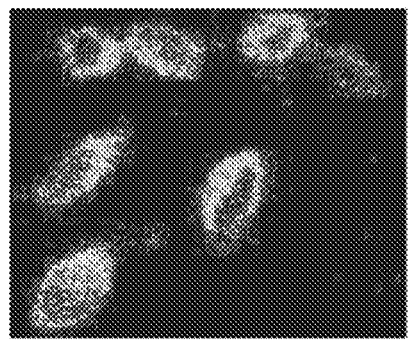
PC-3 120mins
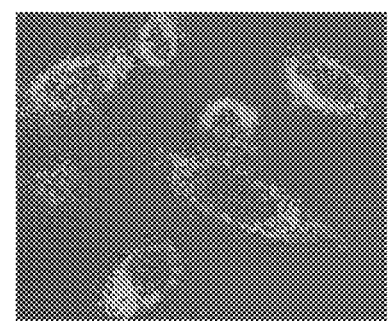
HCT-116 30 mins
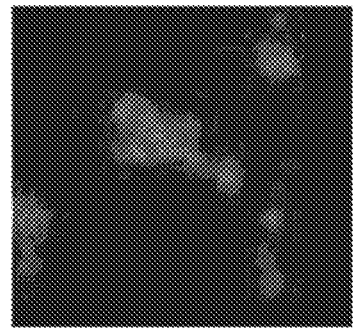
FIG. 7

TARGETED CONTRAST AGENTS AND METHODS FOR TARGETING CONTRAST AGENTS

CROSS-REFERENCE TO RELATED APPLICATIONS

This application is a continuation of co-pending U.S. patent application Ser. No. 11/530,398, filed on Sep. 8, 2006, entitled "TARGETED CONTRAST AGENTS AND METHODS FOR TARGETING CONTRAST AGENTS," the contents of which is incorporated by reference herein in its entirety.

U.S. patent application Ser. No. 11/530,398, filed on Sep. 8, 2006, entitled "TARGETED CONTRAST AGENTS AND METHODS FOR TARGETING CONTRAST AGENTS," claims the benefit of and priority from U.S. Provisional Application No. 60/715,493, filed on Sep. 9, 2005, entitled, "TARGETED CONTRAST AGENTS AND METHODS FOR TARGETING CONTRAST AGENTS," and is a continuation-in-part of U.S. patent application Ser. No. 11/457,370, filed on Jul. 13, 2006, entitled "CONTRAST AGENTS AND METHODS FOR PREPARING CONTRAST AGENTS," now U.S. Pat. No. 8,173,105, issued on May 8, 2012, entitled "CONTRAST AGENTS AND METHODS FOR PREPARING CONTRAST AGENTS," the contents of which is incorporated by reference herein in its entirety.

U.S. patent application Ser. No. 11/457,370, filed on Jul. 13, 2006, entitled "CONTRAST AGENTS AND METHODS FOR PREPARING CONTRAST AGENTS," claims the benefit of and priority from expired U.S. Provisional Application No. 60/699,409, filed on Jul. 13, 2005, entitled, "CONTRAST AGENTS AND METHODS FOR PREPARING CONTRAST AGENTS," the contents of which is incorporated by reference herein in its entirety.

SEQUENCE LISTING

This application contains a sequence listing filed in electronic form as an ASCII.txt file entitled 220702_1100_ST25.txt, created on Sep. 14, 2009. The content of the sequence listing is incorporated herein in its entirety.

BACKGROUND OF THE INVENTION

1. Technical Field

This invention generally relates to diagnostic imaging and novel contrast agent preparations and their use in diagnostic imaging, and more particularly relates to targeted contrast agents and methods for targeting contrast agents to cells and tissues for selective accumulation and retention in magnetic resonance imaging, for example, in visualizing tissue.

2. Prior Art

Imaging technology, including magnetic resonance imaging (MRI), has a vital role in the detection and treatment of cancer lesions and other illnesses. For example, MRI technology provides a powerful, non-invasive tool to map and explore the structure and function of soft tissues. In fact, MRI through the use of high-strength magnets and radio-frequency signals can produce three-dimensional images of tissues. With the improvements in the mechanical imaging system, it is possible to detect neoplastic lesions. However, the detection of early tumor lesions and metastases still remain challenging.

MRI contrast agents have been used to improve the intrinsic contrast of the images from imaging technology. This method relies on the administration of contrast agents to amplify the contrast in imaging between the pathological tissue and the normal tissue. The most widely used class of MRI contrast agents such as diethylenetriaminepentaacetate (DTPA) are based on gadolinium ion ($Gd^{3+}$), manganese ion ($Mn^{2+}$), and iron ion ($Fe^{3+}$) chelates that are strictly extracellular low molecular weight compounds with T1 reflexivity. Ultimately, the efficacy of a contrast agent depends on both the inherent capability to improve images and the pharmacokinetics.

For example, the $Gd^{3+}$ based contrast agents approved for clinical use are mainly non-specific small molecules. Such $Gd^{3+}$ contrast agents usually have relaxivities of <10 $mM^{-1}s^{-1}$ which are 20 to 50 fold lower than the predicted values. The relaxivities are mainly limited by the rotational correlation time of the molecule. The most commonly used contrast agent, DTPA, has a R1 relaxivity of 5 $mM^{-1}s^{-1}$. With this relaxivity, a robust clinical examination usually requires a large dose (>0.1 mM local concentration) in order to reach sufficient contrast or to produce an acceptable image. In addition, this class of contrast agents has a very short circulation time that limits the time window for data collection. Efforts to improve such contrast agents have included the covalent or the non-covalent linkage of the small $Gd^{3+}$ agent to the macromolecules, such as dendrimers or copolymers.

Although considerable progress has been made in the field of contrast agents, contrast agents that can be targeted effectively to specific cells and tissues are still lacking. While the delivery of contrast agents is one of the more important issues, there has been a lack of development of MRI contrast agents able to target specific molecular markers. While many tissue specific contrast agents demonstrate favorable relaxation properties, such contrast agents tend not be designed to recognize specific cellular markers.

Accordingly, there is always a need for improved contrast agents that may be targeted to specific tissues. There also is a need for protein-based contrast agents, capable of being targeted, with wide applicability in molecular imaging of various tissues, tumors, cancers, and diseases. There also is a need for safer contrast agents. It is to these needs among others that this invention is directed.

BRIEF SUMMARY OF THE INVENTION

Briefly, this invention is directed to a novel group of contrast agents that may be targeted to specific cells for improved diagnostic imaging. More particularly, this invention is directed to a class of magnetic resonance imaging contrast agents that targets and accumulates in specific cells and tissue. The novel contrast agents comprise a targeting moiety that can be any peptide or protein or small molecules and a contrast protein that is preferably a contrast agent and can be an organic polymer such as a protein having at least one metal ion binding site capable of chelating paramagnetic and heavy metal ions.

The contrast agents can be developed by operatively linking or incorporating a contrast protein and a targeting moiety or molecule. As contrast proteins suitable with this invention often inherently function as contrast agents, it is preferred that the contrast protein and the targeting moiety or molecules are linked or incorporated in a manner that does not denature the contrast protein, e.g. by linking the targeting moiety or molecules at the C- or N-terminal of the protein-based contrast agent. In one embodiment, the resulting protein is a contrast agent that can bind to the surface of specific cells, and can be endocytosed by those specific cells.

One advantage of targeted contrast agents is that they may provide a safer method to deliver contrast agents. Specifically, the more efficient targeting and uptake of the contrast agent by the targeted cell or tissue may provide for less exposure of the contrast agent to normal cells. As contrast proteins, due in part to the heavy metal, are usually toxic, it may be optimal to reduce exposure of normal cells to contrast proteins. In one embodiment, the contrast agent can bind to target cells and be endocytosed by the targeted cell. Thus, by delivering the contrast agent to only specific cells and tissues, it may be possible reduce exposure of normal cells to contrast agents and heavy metals.

These features, and other features and advantages of the present invention, will become more apparent to those of ordinary skill in the relevant art when the following detailed description of the preferred embodiments is read in conjunction with the appended drawings in which like reference numerals represent like components throughout the several views.

BRIEF DESCRIPTION OF THE DRAWINGS

FIG. 2 is a table of targeting moieties suitable with this invention.

FIGS. 4A-4F are confocal microscopic images obtained by immunofluorescence staining showing the contrast agents are targeted to specific cells and internalized over time.

FIG. 7 shows EGFP-CA1.CD2-a-Bom10 with EGFP fused to the CA1.CD2 N-terminal and bom targeting sequence at the C-terminal of the contrast agent CA1.CD2.

DEFINITIONS

Figure 1:
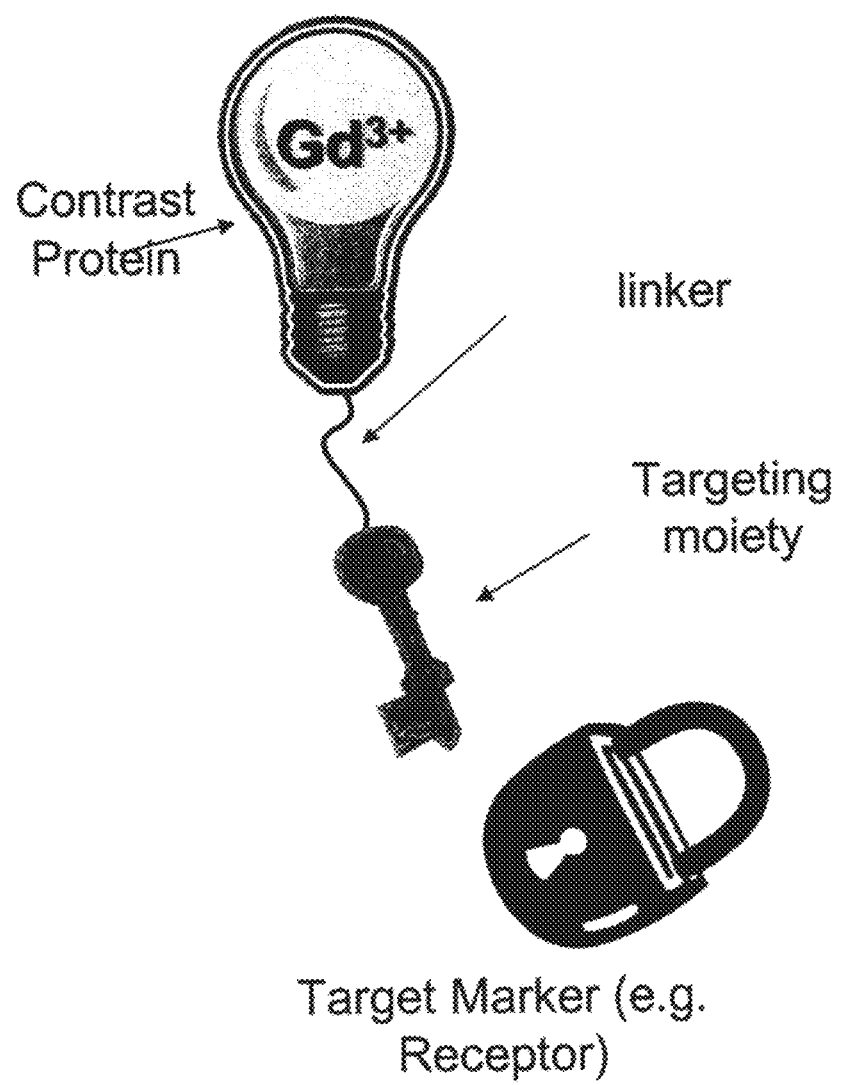
FIG. 1 is a schematic diagram of a targeted contrast agent according to one embodiment of this invention.

Unless specifically indicated otherwise, all technical and scientific terms used herein have the same meaning as commonly understood by those of ordinary skill in the art to which this invention belongs. For purposes of the present invention, the following terms are defined.

The term "nucleic acid molecule" or "polynucleotide" refers to a deoxyribonucleotide or ribonucleotide polymer in either single-stranded or double-stranded form, and, unless specifically indicated otherwise, encompasses polynucleotides containing known analogs of naturally occurring nucleotides that can function in a similar manner as naturally occurring nucleotides. For example, this term can refer to single and double stranded forms of DNA or RNA. Nucleic acid sequences are readily apparent from amino acid sequences.

The term "recombinant nucleic acid molecule" refers to a non-naturally occurring polynucleotide containing two or more linked polynucleotide sequences. A recombinant nucleic acid molecule can be produced by recombination methods, particularly genetic engineering techniques, or can be produced by a chemical synthesis method. A recombinant nucleic acid molecule can encode a fusion protein, for example, a fluorescent protein linked to a polypeptide of interest. The term "recombinant host cell" refers to a cell that contains or can express a recombinant nucleic acid molecule.

The term "encoding" in the context of a polypeptide refers to the transcription of the polynucleotide and translation of the mRNA produced therefrom. The encoding polynucleotide is considered to include both the coding strand, whose nucleotide sequence can be identical to an mRNA, as well as its complementary strand. It will be recognized that encoding polynucleotides are considered to include degenerate nucleotide sequences, which encode the same amino acid residues. Nucleotide sequences encoding a polypeptide can include polynucleotides containing introns and exons. Nucleic acid sequences are readily apparent from amino acid sequence and vice versa.

The term "control sequences" refer to polynucleotide sequences that are necessary to effect the expression of coding and non-coding sequences. Such control sequences can include a promoter, a ribosomal binding site, and a transcription termination sequence. The term "control sequences" is intended to include, at a minimum, components whose presence can influence expression and can also include additional components whose presence is advantageous. For example, leader sequences and fusion partner sequences are control sequences.

The term "operatively incorporated" or the like refers to polypeptide sequences that are placed in a physical and functional relationship to each other. In a most preferred embodiment, the functions of the polypeptide components of the chimeric molecule are unchanged compared to the functional activities of the parts in isolation. For example, a fluorescent protein can be fused to a polypeptide of interest and in the fused state retain its fluorescence while the polypeptide of interest retains its original biological activity.

The term "operatively linked" or the link refers to a juxtaposition wherein the components so described are in a relationship permitting them to function in their intended manners. A control sequence operatively linked to a coding sequence is ligated such that expression of the coding sequence is achieved under conditions compatible with the control sequences.

The term "brightness," with reference to a fluorescent protein, is measured as the product of the extinction coefficient (EC) at a given wavelength and the fluorescence quantum yield (QY).

The term "probe" refers to a substance that specifically binds to another substance (a "target"). Probes include, for example, antibodies, polynucleotides, receptors and their ligands, and generally can be labeled so as to provide a means to identify or isolate a molecule to which the probe has specifically bound.

The term "polypeptide" or "protein" refers to a polymer of two or more amino acid residues. "Polypeptides" or "proteins" are polymers of amino acid residues that are connected through amide bonds. As defined herein, peptides are inclusive of both natural amino acids and unnatural amino acids (e.g. beta-alanine, phenylglycine, and homoarginine). While amino acids are alpha-amino acids, which can be either of the L-optical isomer or the D-optical isomer, the L-optical isomers are preferred. Such amino acids can be commonly encountered amino acids that are not gene-encoded, although preferred amino acids are those that are encodable.

The term "isolated" or "purified" refers to a material that is substantially or essentially free from components that normally accompany the material in its native state in nature. Purity generally can be determined using analytical chemistry techniques such as polyacrylamide gel electrophoresis, high performance liquid chromatography, and the like. A polynucleotide or a polypeptide is considered to be isolated when it is the least predominant species present in a preparation.

The term "naturally-occurring" refers to a protein, nucleic acid molecule, cell, or other material that occurs in nature. A naturally occurring material can be in its form as it exists in nature, and can be modified by the hand of man such that, for example, it is in an isolated form.

Two or more amino acid sequences or two or more nucleotide sequences are considered to be "substantially identical" or "substantially similar" if the amino acid sequences or the nucleotide sequences share at least 80% sequence identity with each other, or with a reference sequence over a given comparison window. Thus, substantially similar sequences include those having, for example, at least 85% sequence identity, at least 90% sequence identity, at least 95% sequence identity, or at least 99% sequence identity.

Two or more amino acid sequences or two or more nucleotide sequences are considered to be "similar" if the amino acid sequences or the nucleotide sequences share at least 50% sequence identity with each other, or with a reference sequence over a given comparison window. Thus, substantially similar sequences include nucleotide sequences considered to be "substantially identical" or "substantially similar".

The term "fluorescent properties" refers to the molar extinction coefficient at an appropriate excitation wavelength, the fluorescence quantum efficiency, the shape of the excitation spectrum or emission spectrum, the excitation wavelength maximum and emission wavelength maximum, the ratio of excitation amplitudes at two different wavelengths, the ratio of emission amplitudes at two different wavelengths, the excited state lifetime, or the fluorescence anisotropy.

The term "fluorescent protein" refers to any protein capable of light emission when excited with an appropriate electromagnetic energy. Fluorescent proteins include proteins having amino acid sequences that are either natural or engineered, such as the fluorescent proteins derived from *Aequorea victoria* fluorescent proteins.

The term "mutant" or "variant" is used herein in reference to a fluorescent protein that contains a mutation with respect to a corresponding wild type fluorescent protein. In addition, reference is made herein to a "spectral variant" or "spectral mutant" of a fluorescent protein to indicate a mutant fluorescent protein that has a different fluorescence characteristic with respect to the corresponding wild type fluorescent protein.

DETAILED DESCRIPTION OF THE PREFERRED EMBODIMENTS

Embodiments of this invention include contrast agents capable of enhancing image contrast by affecting water molecule proton relaxation rates. Such contrasts agents are effective for magnetic resonance imaging, in part, because the water proton relaxation rate in the target tissue is affected differently from the relaxation rate of the water protons in the surrounding tissue. The contrasts agents as disclosed herein are paramagnetic species, which form complexes with metal ions, so to alter the relaxation rates of adjacent nuclei.

More particularly, embodiments of this invention are a novel group of diagnostic contrast agents that are able be targeted to and accumulated in specific cells, such as tumor or angiogentic cells. Preferred embodiments of this invention are a class of magnetic resonance contrast agents that are able to be accumulated in specific cells and tissue.

As schematically shown in FIG. 1, these novel contrast agents comprise (a) a targeting moiety that can be any peptide or protein or small molecule that is able to target the contrast agent to specific cells and tissue, (b) a contrast protein that is a contrast agent itself and an organic polymer such as a protein having at least one metal ion binding site capable of chelating paramagnetic and heavy metal ions, and (c) an optional linker between the contrast protein and the targeting moiety.

More specifically, the targeting moieties useful with this invention include sequences that allow the contrast agent to bind to proteins or other targets, which increase the concentration of the contrast agent at a site to be imaged. In one embodiment, the targeting moiety can be a molecule or sequence suitable to target certain receptors or cells. Further, these targeting sequences can include sequences for diseased cells. For example, Bombesin/GRP for GRP receptor can be suitable for targeting the contrast agent to cancer cells. The particular targeting moiety useful with this invention can be dependant on the nature of the target and the specific requirements of the binding.

Further, the contrast protein can have inherent contrast properties. In one embodiment, this invention can be useful with a novel group of diagnostic contrast agents having tuned properties, even more particularly, to a class of magnetic resonance contrast agents that accumulates in tissue. These novel contrast agents comprise (a) a scaffold protein that can be an organic polymer such a protein and (b) at least one tailored metal ion binding site capable of chelating paramagnetic and heavy metal ions, wherein the at least one tailored metal ion binding site is integrated into select folding pockets within the scaffold protein. However, it is understood that any protein based contrast agent can be used with this invention.

Further, the contrast agents of certain examples can include an optional linker through which the targeting moiety is attached the scaffold protein. The optional linkers preferable have flexibility so that both the contrast moiety and target moiety have functional properties. These linkers can vary in lengths and, for example, can include different lengths and amino acid sequences. Exemplary linkers include small subunits comprising 1 to 30 carbon atoms covalently connected by single or multiple bonds In one embodiment, the contrast agents disclosed herein can be developed by operatively linking a contrast protein and a targeting moiety or molecule. More specifically, the contrast protein and the targeting moiety or molecule are linked in a juxtaposition type relationship permitting them to function in their intended manners. As contrast proteins suitable with this invention often inherently function as contrast agents, it is preferred that the contrast protein and the targeting moiety be linked in a manner that does not denature the contrast protein. The resulting protein is a contrast agent that can be accumulated in specific cells.

Preferably, the contrast protein and the targeting moiety are operatively linked through a peptide bond. In one embodiment, the targeting moiety and the contrast protein are ligated by linking or fusing the targeting moiety at the C- or N-terminal ends of the contrast agent through a peptide bond. By attaching or fusing the targeting moiety at a terminal end, the contrast protein can be targeted to specific cells while maintaining functionality of the contrast protein and the structural integrity of the targeting moiety. In this embodiment, the contrast agent can be expressed as a single protein. Further, amino acids, e.g, glycine can be added the terminal ends to help ensure a more stable structure.

Further, the contrast protein and targeting moiety are operatively linked to residues by other type of covalent bonds to allow the additional modifications such as phosphorylation, glycosylation and methylation with better binding specificity and affinity.

Furthermore, the targeting moiety can be operatively linked to or incorporated within residues within the contrast protein. In this embodiment, the targeting moiety can be incorporated to the contrast protein such that the contrast protein continues to function as a contrast protein. For example, the targeting moiety can be grafted into the loop region of the contrast protein. This embodiment can result in a contrast agent with an more active binding configuration since the N- or C-terminal attachments have less structural influence. In addition, this targeting moiety can be grafted at the loop region of the protein contrast moiety to ensure a better conformation. In this case, two flexible linkers flanking both ends of the targeting moiety are preferred. In addition, the grafted target sequence can be more stable and less susceptible to cleavage or degradation by amino- or carboxyl peptidases.

In one embodiment, the targeting moiety may be selected for the ability to interact with a receptor expressed on specific types of cells or tissue and to induce endocytosis. For example, such cells may be targeted to cell biomarkers or cancer biomarkers which are specific receptors expressed on the surface at specific densities. Further, these receptors or biomarkers are shown in the literature and are consistently being discovered and reported thereon. One of ordinary skill in the art may select targeting peptides without undue experimentation by reviewing the literature to finding peptides that can bind and induce endocytosis in specific types of cells.

In one example, the targeting moiety can be part of the gastrin release peptide (GRP) that can bind to specific type of cell surface receptors that are highly expressed in cancer cells or tissue, i.e. GRP receptors. While GRP receptors are cancer biomarkers and are expressed in a number of neuroendocrine tumors, GRP receptors are not highly expressed in normal tissue. More particularly, GRP receptors, which are expressed in neoplastic transformed prostate and breast tissue, can be selected targets of the contrast agent to transformed prostate and breast tissue. As such, a contrast agent having both a contrast protein and GRP target sequence can be bound to such cancer cells and induce endocytosis, which results in more contrast agent in cancer cells and an improved MR images.

Other suitable targeting moieties are peptides or proteins that are able to bind to specific types of cells or tumors and induce endocytosis in the cells. Such targeting moieties may be ligands that can target receptors on specific cancers and can include cholecystokinin, growth hormone-releasing peptide, prolactin, cytokines, neurotransmitters, neuromodulators, EGF receptors and TNF receptors (see, e.g., FIG. 2). For example, the targeting moiety may be somatostatin, which can target somatostatin receptors subtypes sst1-5 found in human neuroendocrine tumors and other lymphomas. Other suitable targeting moieties may be small molecules such as folic acid or carbohydrates, phosphorylated peptides and glycoproteins or peptides. Suitable ligands and their respective receptors are shown in FIG. 1. Exemplary targeted contrast agents that can be created accordingly are shown in Sequences ID Nos. 14-26.

It is possible to operatively link or integrate more than one targeting moiety to the contrast protein. By operatively linking more than one target sequence to the contrast protein, it is possible to create a contrast agent with greater specificity for specific cells or cancer cells by providing more than one type of molecular interaction for recognition of the specific cells or cancer cells. In addition, the binding affinity and contrast effect can be increased by adding more than one target peptide (can be tandem repeats) and increase local effective concentrations.

The target specificity of the contrast agent arises by the propensity of the contrast agent to trigger receptor mediated endocytosis. The binding of the targeting moiety to the receptor can trigger receptor mediated endocytosis, which begins with the invagination of specialized regions of the plasma membrane called coated pits. Clathrin then forms a lattice around the coated pit to form vesicles, which fuse with endosomes. The contrast agent then is released into the cell from the endosome. The contrast agent accumulates within targeted cells and tissues.

The contrast properties of the contrast agent disclosed herein arise in part from the ability of the contrast protein to function as a contrast agent independently from the targeting moiety. Preferably, the contrast protein is an organic polymer such a protein having at least one metal ion binding site capable of chelating paramagnetic and heavy metal ions and can function as a contrast agent. Such contrast proteins may be constructed or modified prior art contrast agents or may be newly constructed agents. Exemplary protein based contrast agents that may be used with the present invention include domain 1 of CD2 and green fluorescent protein (GFP). As will be discussed later in more detail, the novel contrast agents are in many cases known contrast agents that are directed to specific cells through the use of a targeting moiety.

The contrast agents of the present invention may be formulated with conventional pharmaceutical or veterinary mechanisms and materials. The contrast agent compositions of the present invention may be in conventional pharmaceutical administration forms such as powders, solutions, suspensions, dispersions, etc.; however, solutions, suspensions and dispersions in physiologically acceptable carrier media, for example water for injections, will generally be preferred. For example, such materials include emulsifiers, fatty acid esters, gelling agents, stabilizers, antioxidants, osmolality adjusting agents, buffers, preservatives, antimicrobial agents, and pH adjusting agents. Further, delivery mechanisms include parenteral administration (injection or infusion directly). The compositions according to the invention may therefore be formulated for administration using physiologically acceptable carriers or excipients in a manner fully within the skill level of the art.

In use and operation, the contrast agent may be targeted or accumulated in specific cells or tissues. The targeting moiety, as part of the contrast agent, may associate with receptors present on cells (or surfaces thereof) and induce endocytosis therein. Specifically, the binding of the contrast agent, particularly the targeting moiety to a receptor or transport protein on the membrane of cells, can induce endocytosis of the receptor along with the contrast agent. The process of endocytosis effectively internalizes an amount of the contrast agent. As any contrast agent that does not bind and subsequently endocytose will likely be excreted, the contrast agent may be accumulated in cells or tissues with the specific receptor or transport protein.

The contrast agents can be administered in doses effective to achieve the desired affects. Such doses can vary widely, depending upon the contrast agent employed, the organs or tissues to be imaged, the imaging equipment being used, and the like. The diagnostic compositions of the invention are used in the conventional manner. The compositions may be administered to a patient, typically a warm-blooded animal, either systemically or locally to the organ or tissue to be imaged, and the patient then subjected to the imaging procedure.

To overcome immunogenicity, the contrast agent may be modified for use with the specific organism by those with ordinary skill in the art. For example, where the contrast agent in used in rats, the contrast agent may be modified by incorporating the rat self sequence.

The rate of infusion of the contrast agent can be matched with the rate of cellular uptake to optimize cellular accumulation of the contrast agent in the tissue or cell. Efficiency of the contrast agent delivery to cellular targets can be generally dependant on the rate of vascular extravastion and pharmacokinetics of the contrast agent in plasma.

One of the bioelimination routes for the contrast agents of this invention can be renal. The macrostructure is eventually abstracted by the RES and it is preferred that chelate attachment is via biodegradable bonds that on cleavage release fragments that are renally excretable, e.g. with a molecular weight of less than 60 KD, preferably less than 10 KD, especially 200 to 5000 D. To alter the bioelimination route, a fusion protein or a non-degradable particle moiety can be added to the protein contrast agent with a flexible linker.

One advantage of this invention is that it may provide a safer method to deliver contrast agents. Specifically, the more efficient targeting and uptake of the contrast agent by the targeted cells or tissue may provide for less exposure of the contrast agent to normal cells. As contrast proteins, due in part to the metal ion, are usually toxic, it may be optimal to reduce exposure of normal cells to contrast protein.

I. Protein Based Contrast Agents

This invention can be useful with a novel group of diagnostic contrast agents having tuned properties and, even more particularly, to a class of magnetic resonance contrast agents that accumulates in tissue. These novel contrast agent comprises (a) a scaffold protein that can be an organic polymer such a protein and (b) at least one tailored metal ion binding site capable of chelating paramagnetic and heavy metal ions, wherein the at least one tailored metal ion binding site is integrated into select folding pockets within the scaffold protein.

The novel contrast agents can be developed by designing tailored binding sites and operatively integrating these sites into scaffold proteins. As will be discussed later in more detail, the binding site may be developed by a design approach or by a grafting approach. After the site has been developed, the site or sites are operatively integrated into the select areas of the scaffold protein. The contrast agent then may be administered to animals or humans through known delivery methods.

In illustrative embodiments, at least one of the metal chelating sites is embedded in the scaffold protein. In such an embodiment, the metal chelating site can be placed within the scaffold protein such that the metal chelating sites are within the interior of the contrast agent. Preferably, at least one of the metal chelating sites is embedded using amino acids of the scaffold proteins as ligands to chelate the metal ion. More preferably, the at least one metal binding site is embedded within the protein such that the scaffold protein has a correlation at least in part resembling the protein itself.

In illustrative embodiments, the scaffold protein for MRI applications is a protein that will host the tailored metal ion binding sites and has the following characteristics:

(a) stability in a physiological environment against cleavage and denaturation;

(b) a topology suitable for the integration of metal ion sites;

(c) a rotational correlation time optimized for the magnetic field (e.g. around 100 milliseconds in a magnetic flied of 1.3 to 3 T), e.g. higher magnetic field application can prepared by changing the site of the protein; and (d) a water exchange rate such that the relaxivity of the protein is not limited by the water exchange rate.

Preferred properties of the scaffold protein also may include water solubility, low interaction with the other cellular metal ions and low toxicity. While of all these properties are not required, the optimal properties of the scaffold protein can and do depend on the specific parameters of the imaging application.

One important property of the scaffold protein is its ability to accept the introduction of metal ion binding sites therein. Preferably, the scaffold protein has a folded conformation, a three-dimensional structure or an amino sequence with some homology to the proteins whose structure has been solved at least in part. For example, the scaffold protein can be screened to determine whether it can tolerate the integration of various binding sites without excessive denaturation. For example, the integration of metal ion binding sites into the scaffold protein should not denature or unfold the protein. Thus, the metal ion binding site should not be placed by mutating a hydrophobic core or in a position that results in substantial structural perturbation. This can be examined by sequence alignment of proteins in the same family. Preferably, the amino acids that have an essential role in folding of the structure or the function will be conserved among different species of this same type of the protein.

In another embodiment, the scaffold protein can be a natural protein that chelates a metal ion. In such embodiments, it is possible to modify the natural metal binding sites to chelate heavy metals or paramagnetic metals or other metals useful in diagnostic imaging. For example, it is possible to tailor the amino acid sequence of the scaffold protein that ordinarily binds $Ca^{2+}$ to bind $Gd^{3+}$ by modifying nitrogen or oxygen molecules contained therein.

Preferably, metal ion binding sites are placed into a scaffold protein such that the metal is able to be tumbled together with the protein. It is better to find a location that is not as flexible as or is the same flexibility as the protein body so as to match the correction time. In this case, it is preferred to design or create the binding pocket in the protein. Although insertion also should work, it is preferable to do so in a relatively not so flexible region. Usually the protein can be checked by looking at the B factor (temperature factor for X-ray) or $S^2$ factor (dynamic flexibility factor for NMR) of the pdb (protein data bank) file of the structure.

More than one metal binding site may be integrated into a scaffold protein. The inclusion of more than one binding site improves the sensitivity of the contrast agent. Further, in cases where more than one binding site is integrated into the protein, the site could have different affinities but should still have strong enough affinity for the selected metal so to avoid competition with physiological metal ions. Both metal ions should be embedded into the host protein with preferred rotational correlation times and water exchange rates to provide MRI contrast with an increased sensitivity.

In preferred embodiments, the contrast agents can have a high affinity to and can preferentially select a particular metal ion (e.g. $Gd^{3+}$, $Mn^{2+}$ or $Fe^{3+}$). In one example, exemplary contrast agents showed a dissociation constant $K_d$ less than $10^8$ [M] for $Gd^{3+}$ in an environment having physiological metal ions and prevented those metal ions from precipitation under physiological conditions. Thus, the present invention may be used to create contrast agents having optimal selectivity for a specific metal ion.

The present invention can provide a new mechanism to increase the relaxivity of contrast agents. This is accomplished by designing the metal ion binding sites, e.g. $Gd^{3+}$, in proteins, which can eliminate the mobility and flexibility of the chelating moiety associated with currently available contrast agents. More particularly, by tailoring the binding site, it is possible to prepare contrast agents with higher relaxivity. High proton relaxivity by contrast agents can further enhance images.

Scaffold Proteins.

Scaffold proteins suitable with the present invention include proteins or organic polymers containing amino acids. Such scaffold proteins are inclusive of both natural amino acids and unnatural amino acids (e.g. beta-alanine, phenylglycine, and homoarginine). While amino acids are alpha-amino acids, which can be either of the L-optical isomer or the D-optical isomer, the D-optical isomers may be preferred, as such isomers are less subject to proteolytic degradation. Such amino acids can be commonly encountered amino acids that are not gene-encoded, although preferred amino acids are those that are encodable.

Various scaffold proteins may be used according to the invention but in general they will be proteins, terminally modified proteins, and organic polymers. More specifically, suitable scaffold proteins can be selected with properties suitable for diagnostic applications. The scaffold protein for use with this invention may be of unitary construction (a particulate, a polychelant or a dendrimeric polymer). Scaffold proteins suitable with this invention may be selected without undue experimentation.

The scaffold protein also can be a natural protein that ordinarily binds a metal ion. In such embodiments, it is possible to modify the natural metal binding sites to chelate heavy metals or paramagnetic metals or other metals useful in diagnostic imaging. For example, it is possible to tailor the amino acid sequence of the scaffold protein that ordinarily binds $Ca^{2+}$ to bind $Gd^{3+}$ by modifying amino acid ligand residues contained therein. For example, one can modify the binding sites in alpha-lactalbumin to bind $Gd^{3+}$. For another example, it is possible to modify EF-hand calcium binding sites in proteins such as calmodulin to bind $Gd^{3+}$ (e.g. CA9.CD2).

In illustrative embodiments, a scaffold protein can be selected for the following criteria:

1) Exhibition of strong stability in terms of resistance to pH denaturation and resistance to proteolytic cleavage.

2) The availability of structural information about the protein. If less structural information is available, which allows for the rational design of metal binding sites with optimized inner, secondary and outer sphere relaxation and metal binding properties, then structure prediction can allow for the modification of the protein.

3) Tolerance of mutations without sacrificing native conformation and folding.

4) The molecular sizes are suitable for the particular application. An optimal size can be dependant on a particular diagnostic application. For example, a compact structure, e.g. molecular weights between 11-30 KDa, and rotational correlation times of ~10-30 ns, can be an optimal size for may particular diagnostic applications. Further, a molecular size can improve circulation retention times and tissue penetration. For example, stronger in vivo kidney images and prolonged retention time can allow for more detailed imaging of the renal system for diagnosing kidney diseases such as renal carcinoma and can allow for more precise measurement of blood flow and volume. Further, a proper size of the protein frame can provide improved tissue penetration and molecular targeting, which can be a limitation of some the large size of dentrimers, nano-particles, and superparamagnetic particles.

5) Optionally, the scaffold protein also can have intrinsic properties, which can allow for the construction of multi-functional probes and use of fluorescence as a tool to assist in the design of MRI contrast agents for molecular imaging without the need of other fluorophores.

Suitable proteins include proteins from immunoglobulin G (IgG) superfamily such as CD2 proteins (a cell adhesion protein) that exhibit high stability against proteolysis, thermal conditions (Tm 67 C), pH (2-10), and salt (0-4 M NaCl) denaturation. CD2 proteins can be suitable with this invention because such proteins are stable in physiological environments, have a topology suitable for the integration of at least one or multiple metal ion chelating sites, and typically have a relaxivity greater than 10 $mM^{-1}s^{-1}$ (some of them up to about 50 $mM^{-1}s^{-1}$). In addition, CD2 can tolerate multiple surface mutations without unfolding the protein. Other research has shown that CD2 can be used as a host protein to design calcium binding sites. Examples using CD2 are described below.

Fluorescent proteins are another class of preferred scaffold protein for this invention, as these proteins are stable in a physiological environment against proteolytic degradation and pH denaturation (pH 5-10). Such fluorescent proteins include an array of fluorescent proteins including those related to *Aequorea*. Suitable fluorescent proteins should have a useful excitation and emission spectra and may have been engineered from naturally occurring *Aequorea victoria* green fluorescent proteins (GFPs). Such modified GFPs may have modified nucleic acid and protein sequences and may include elements from other proteins. The cDNA of GFPs may be concatenated with those encoding many other proteins—the resulting chimerics are often fluorescent and retain the biochemical features of the partner proteins. Yellow fluorescent proteins, blue fluorescent proteins and red fluorescent proteins also can be used as the scaffold proteins for contrast agents. Such proteins also are included in the invention.

Other suitable proteins include extra cellular receptors and growth factors that are known to be stable against protein cleavage. In addition, proteins from four-helical bundle family (such as Rop), the maltose binding protein family, and thioredoxin family have been shown to accept mutations and metal binding sites. While the inventors have not tested every protein for suitability as a scaffold protein, the diverse array of examined proteins demonstrates this invention includes all of the proteins having the criteria disclosed herein. It is contemplated that one of ordinary skill in the art can develop and select a suitable scaffold protein based using ordinary research techniques and the criteria disclosed herein.

One advantage of using fluorescent proteins is that contrast agents constructed from such proteins can be multi-functional probes. In such an embodiment, the contrast agent constructed from fluorescent proteins can be screened using both fluorescence and MR imaging. This can be extremely advantageous as such properties equip the contrast agent with both the fluorescence needed for fluorescence detection methods and the sensitivity needed for the deep tissue detection from MRI. Such contrast agents are multifunctional contrast agents.

Other proteins may be used as scaffold proteins for this invention. Preferably, scaffold proteins are able to tolerate the addition of the metal ion binding site without substantial disruption to its structure. One of ordinary skill in the art can select a scaffold protein based on preferences without undue experimentation.

Metal Ion Binding Sites

The affinity of the metal ion binding site may vary the contrast agent affinity for metal ions. Specifically, as affinity and sensitivity of the metal ion binding sites may be modified, the relaxivity and metal affinity of the contrast agent may be modified. Preferably, the metal ion binding site has optimal imaging properties including metal binding affinity, selectivity, relaxivity, nuclear magnetic relaxation dispersion (NMRD) profile, and water exchange rates.

One of ordinary skill in the art can use methods known in the art or developed hereafter to develop a metal binding site having optimal characteristics. For example, the metal ion binding site of the present invention can be constructed at least using these methods:

(1) A computational design approach in which the metal ion binding site with a selectivity and affinity for a metal ion is engineered and rationally designed de novo based on optimal binding characteristics of metal ion with other moieties;

(2) A grafting method in which the metal ion binding site with a selectivity and affinity for a metal ion is engineered and constructed selectively by varying the primary, secondary, tertiary, and/or quaternary structures of an identified binding site; and (3) Other methods known or developed hereafter and a combination of methods known or developed hereafter.

1. The Computational Design Approach

The computational design approach focuses on designing a metal ion binding site de novo. This design approach focuses on using an algorithm to construct and engineer an optimal binding site. Preferably, the computation design approach is used to create optimal binding sites by, e.g., varying the coordination geometry of the site, the water number in the coordination shells, the ligand types, and the charges.

The computational design approach comprises the following steps:

(1) Accessing one or more databases having structural, coordination, and/or 3-dimensional structures or models of metal ion binding sites, or creating model structures based on the sequence homology to other metal binding sites;

(2) Generating one or more preliminary metal ion binding sites from portions of the structural data;

(3) Selecting rationally one or more suitable metal ion binding sites from the generated preliminary binding sites based on, e.g., coordination geometry; and (4) Creating a metal ion binding site by tailoring and tuning the selected metal ion binding site.

The metal ion binding site may be incorporated into a scaffold protein, e.g. a fluorescent or CD2 protein. Further, such a method may be used to alter metal ion binding properties of proteins and generate new materials with various ion binding affinities.

More particularly, the method involves searching and accessing public and or private databases for preferred components of a metal ion binding site. Such databases that may be searched for the criteria or components may include public domain banks (e.g. National Center for Biotechnology Information (NBCI) or PubMed of the US National Institution of Health) or knowledge banks such as protein modeling structure data banks (e.g. Cambridge or RCSB Protein Data Bank and BioMagResBank database) or other biotechnological data banks. Further, the database could include structural data from metal ion binding proteins whose structures have been characterized previously. One of ordinary skill in the art can identify databases and sources of material for databases suitable with this invention. Use of a computer with internet or intranet capabilities obviously would greatly speed up the searching and is preferred.

These databases may be used to provide structural analysis of one to several thousand different small molecules or metal ions that bind to a protein. Such analysis may include local coordination properties, types of residues or atoms commonly used to bind a desired metal ion, chemical features (e.g. pKa or changes), the number of charged residues on a site, and the range or deviation of the known binding sites. Further, such analysis may include the environment, such as types of atoms, residues, hydrophobicity, solvent accessibility, shapes of the metal binding sites, electrostatic potentials, and the dynamic properties (e.g. B-factors or the order factors of the proteins) of the binding sites. Such analysis also may include whether a binding site for a particular metal ion is a continuous or discontinuous binding site.

Once preliminary metal ion binding sites are found, using the structural data and analysis, one or more suitable metal ion binding sites may be generated based on rational factors. Specifically, different search algorithms may be used to generate potential metal ion binding sites based on other key features in addition to, for example, the geometric descriptors. These key features include the properties of the original residues in the scaffold protein, ligand positions that are essential to protein folding, the number of the charged residues and their arrangement and number of water molecules in the coordination shell. The hydrogen bond network and the electrostatic interactions with the designed ligand residues also can be evaluated. Furthermore, the protein environments of metal ion binding sites can be analyzed according to solvent accessibility, charge distribution, backbone flexibility, and properties of scaffold proteins. Thus, one of ordinary skill in the art may rationally select a binding site based on desired parameters.

Once the metal ion binding sites are generated, a site may be tailored using two complementary approaches of computational design and grafting (see below). First, as discussed above, the metal ion binding site may be tailored using a grafting method in which the primary, secondary, tertiary, and/or quaternary structures are tuned. Second, the metal ion binding site may be tailored using a computational design approach. It is understood that one or both of these approaches may be used to tailor the binding site.

The computational design approach includes modifying the metal ion binding site by modifying residues in the scaffold of the metal ion binding site. In one embodiment, a geometric or statistical description of the ligands around a metal ion, a three-dimensional structure of the backbone of proteins, and a library of side-chain rotamers of amino acids (or atoms from the main chain) can identify a set of potential metal-binding sites using a computer. Using the geometric and graph description of a particular metal ion site, key ligand residues are carefully placed in the amino acid sequence to form the metal (metal ion) binding pocket. This binding pocket can be created automatically by a computer algorithm designed according to the coordination description and the user's preferred affinity.

The created potential metal ion binding sites can be optimized and tuned to specification. A backbone structure of the metal ion binding site with different degrees of flexibility may be used according to the need or the flexibility of the metal ion binding site. The designed metal ion binding sites are further filtered and scored based on the local factors, which may include the shape of the metal ion binding sites, locations, charge numbers, dynamic properties, the number of mutations needed, solvent accessibility, and side chain clashes. To achieve the maximum relaxivity, it can be important to have one to two oxygen atoms from the solvent water molecules in the coordination shell without reducing the required binding affinity and selectivity.

Stronger metal ion binding affinities of the designed sites may be developed based on several modeled factors that contribute to metal ion affinity. For example, the number of ligand residues is a factor to directly chelate a specific metal ion. In some cases, in order to have a strong metal ion affinity with a $K_d$ necessary to measure a metal ion concentration, it is necessary to include residues from the protein frame for optimal metal ion binding. In other cases, the number of charged residues is able to change metal ion affinity. In still other cases, the ligand type is a factor as the binding preferences of a chelate may depend on the particular ligand type. Other factors, such as negatively charged environments, may contribute to the binding affinity of a metal ion binding protein and can be taken into account by those of ordinary skill in the art without undue experimentation. These charged residues can increase the water-exchange rate to avoid its limitation for the required relaxivity.

An illustrative version of this computational approach is the computerized (or otherwise automated) querying of one or more databases that comprise structural data on metal ion binding sites using selected criteria relevant to the metal ion binding site, generating at least one preliminary metal ion binding site from the database information based on compatibility with the selected criteria, and selecting one or more suitable metal ion binding sites from the preliminary metal ion binding sites based on optimal compatibility with the selected criteria. Once a suitable metal ion binding site is selected, the nucleic acid sequence of the selected metal ion binding site is obtained, tailored, and operatively linked with a scaffold protein sequence, whereby the nucleic acid sequence of the selected metal ion binding site is tailored so to achieve the metal ion binding site having a desired specificity for the metal ion. Further, a nucleic acid sequence encoding the preliminary binding sites can be generated from the structural or model data. The computational approach also can be used to produce the metal ion binding site.

The computational approach can be performed on or by a system comprising at least one database that comprises the structural data on metal ion binding sites, an algorithm for generating the preliminary metal ion binding sites from portions of the structural or model data using selected criteria relevant to the metal ion binding site and rating the preliminary metal ion binding sites based on specificity for a selected metal ion, and a computer for executing the algorithm so as to query the databases to generate the preliminary metal ion binding sites. The algorithm generally is a relatively simple searching algorithm that will query the databases based on inputted criteria.

2. The Grafting Method

The grafting method focuses on engineering and constructing a metal ion binding site by modifying the primary, secondary, tertiary, and/or quaternary structure of an identified binding site. By selectively manipulating the structure of the binding site, it is possible to obtain a metal ion binding site that can be engineered into a scaffold protein, e.g. CD2 or fluorescent protein, without significantly denaturing the protein. Using the grafting method, it is possible to achieve a binding site that has a stronger preference for one metal ion over another metal ion. Such modifications may allow for improved contrast abilities.

Initially, an identified binding site for use with the grafting method may be any continuous sequence site that has some affinity for a metal ion. Such binding sites may derive from either known binding peptides such as an individual EF-hand site or from short fragments that have demonstrated the ability to bind specific metal ions such as alpha-lactalbumin. Such peptides may be highly conserved in nature and prevalent throughout nature or may be unnatural but known to have an affinity for a particular metal ion. One of ordinary skill in the art is able to identify binding sites with affinity for a metal ion without undue experimentation. Once the binding site has been identified, the primary structure of the metal ion binding site may be altered and tuned to achieve a metal ion binding site with improved binding characteristics. For example, more charged ligand residues such as aspartate and glutamate may be engineered by inserting codon(s) into the metal ion binding site so as to tune the responsiveness of the site or the scaffold protein. The inclusion of additional charged ligands can allow the contrast agent to achieve an affinity for selected paramagnetic metal ions and to have a desired selectivity. Additionally, one or two water molecules also can be introduced into the coordination shell by removing or modifying ligand residues and their environments. Further, other mutations to the primary structure include removing or adding amino acids to change properties such as flexibility or rigidity of the site. Adding or removing amino acids from the binding site alters the primary structure of the binding site.

The secondary structure of the metal ion binding site, that is, the spatial arrangement of amino acids residues that are near one another in linear sequence, may be modified to tune the sensitivity and responsiveness of the metal ion binding site. The residues on the site itself, the flanking or the neighboring structures such as helices, beta strands, or turns may be modified by changing properties such as hydrophobicity, salt bridges, secondary structure propensity (e.g. helicity, and β-sheets), and charge interactions with different amino acids, which all may inherently change the secondary structure.

The tertiary structure of the metal ion binding site may be modified to further tune the sensitivity and responsiveness of the metal ion binding site. The affinity of the metal ion binding site for the metal ion may be varied by selectively manipulating and adding helices, loops, bridges and/or linkers and chemical properties such as hydrogen bonding, electrostatic interactions and hydrophobic interactions. In fact, such variations in tertiary structure may add stability and affinity by increasing secondary structure propensity, adding charge interaction of the side chains, and by stabilizing the metal ion binding coordination chemistry. As such, it may be possible to increase or decrease the binding affinity of the continuous binding site by tuning the tertiary structure of the metal ion binding site. In addition, the dynamic properties can be modified by increasing the packing of the protein and replacing residues with amino acids or other moieties with more rigid (e.g. Pro) or flexible (e.g. Gly) properties, or adding disulfide bonds.

One method of directly altering the primary, secondary, and/or tertiary structure of the metal ion binding site is by altering the charges in the site. As the charges in any binding site have a significant role in the structure of the site, changing the charges or charge ratio may have significant impact on the structure of the site. More importantly, as the charged side chains exhibit a strong influence on the metal ion binding affinity even though they are not directly involved as ligands, the variation of these chains results in variations in metal ion binding affinities and selectivity. A metal ion binding site may have stronger affinities to and better selectivity for a desired metal ion over a competitive metal ion by designing or modifying the site, e.g., changing the number of charged ligand residues to form metal ion binding pockets. For example, the metal ion binding affinity of the metal ion binding site may be varied by changing the charged side chains that are present on the metal ion binding site and or the neighboring environment. The replacement of charged residues such as aspartate or glutamate with a residue such as alanine may dramatically reduce the binding affinity for the metal ion by up to 100 times.

In the case of multifunctional contrast agents, e.g. where the contrast agent is a fluorescent protein, it can be important to induce metal binding sites without altering significantly the chromophore environment to reduce the fluorescent/optical signal. These metal binding sites can be added at remote locations away from the chromophore or simple fusion to the fluorescent moieties. Such locations can be evident from the sequence and protein folding.

In other embodiments, the grafting approach may be used with the design approach to create optimal metal binding sites. For example, metal binding sites can be created by using part of a continuous binding site and part of ligand residues created by computer design. The loops or any sequences of the proteins can be removed or modified to achieve optimal required binding affinity, metal selectivity, relaxivity and stability. Thus, by varying the primary, secondary, and/or tertiary structure of the metal ion binding site, it is possible to achieve a metal ion binding site with desired specificity and affinity and more importantly contrast abilities.

3. Other Methods

The metal ion chelating or binding can be developed using methods known or developed hereafter. Such methods include protein engineering methods that are readily available in the art, which include by modifying the existing metal binding sites to change the metal binding specificity and dynamic properties. Such methods also include techniques to modify existing binding sites with protein ligand residues or to fuse protein-contrast agents with other molecules, which include the formation of metal binding sites with other molecules/prosthetic groups including non-natural amino acids or carbohydrates or phosphates. Exemplary methods for protein engineering or for design suitable methods are also disclosed in Barondeau D. P. and Getzoff E. D., Structural Insights into Protein-Metal Ion Partnerships, Current Opinion in Chemical Biology, 2004, 14:7; and Lu, Y, Design and Engineering of Metalloproteins Containing Unnatural Amino Acids or Non-Native Metal-Containing Cofactors, Current Opinion in Chemical Biology, 2005, both of which are incorporated by reference in their entirety.

Further, it is possible to combine methods to prepare desired metal ion chelating sites.

Selecting Metal Ion Binding Sites in the Scaffold Protein

The metal ion binding sites may be selectively introduced into numerous sites of a scaffold protein without substantially impairing its secondary structure. A number of methods for identifying integration sites in proteins, such CD2 proteins, fluorescent proteins (e.g. GFP, YFP, CFP, and RFP) are known in the art, including, for example, site directed mutagenesis, insertional mutagenesis, and deletional mutagenesis. Other methods, including the one exemplified below and in the Examples, are known or easily ascertained by one skilled in art.

The sites of the fluorescent protein that can tolerate the insertion of a metal ion binding site also may be determined and identified by gene manipulation and screening. By generating mutant proteins and by manipulating the DNA sequence, it is possible to obtain a variety of different insertions, which then may be screened to determine whether the protein maintains its intrinsic activities. Preferably, sites that remove or interfere with the intrinsic fluorescence of the fluorescent protein are not optimal and may be screened out. Variants identified in this fashion reveal sites that can tolerate insertions while retaining fluorescence.

The preferred metal ion binding sites for use with scaffold proteins may be selected by considering five criteria so to as optimize the local properties of the metal binding site, the fluorescent protein, and the protein environment. First, the geometry of the metal ion binding site should have relatively minor deviations from the desired coordination geometry. Second, negatively charged residues should be varied by no more than 3-5 charges according to the desired affinity for metal ion ($K_d$). Third, the water coordination shell of the metal ion chelating sites should be able to coordinate at least 1-2 water molecules. Fourth, the residues from the loops between the secondary structures with good solvent accessibility are desired for both the folding of the protein and the fast kinetics required for the contrast agent.

Fifth, the mutation or the introduction of the metal ion binding site should not substantially interfere with the synthesis and folding of the protein. More particularly, the introduction of the metal ion binding site should not interfere with either post-translational chromophore formation or intermolecular interactions required for stabilizing the chromophores and folding of the protein frame. Furthermore, the introduced side chain should not be overpacked and should not clash with the protein frame of the scaffold protein (e.g. the fluorescent protein). The direct use of chromophore residues as chelating sites is not preferred but is within the scope of this invention.

II. Targeting Moieties

The targeting moiety useful with this invention includes sequences that allow the contrast agent to bind to proteins or other targets, which increase the concentration of the contrast agent at a site to be imaged. The particular targeting moiety useful with this invention can be dependant on the nature of the target and the specific requirements of the binding. Examples of useful targeting moieties include drugs, lipophilic or amphiphilic organic molecules, porphyrins, receptor ligands, steroids, lipids, hormones, peptides, oligonucleotides (DNA, RNA or chemically modified versions thereof), carbohydrates or other biomolecules or substances that are known to bind with sufficiently high affinity to one or more components in the specific tissue desired to be imaged. It is contemplated that certain targeting moieties can have a higher affinity for a target than the other targeting moieties.

Targets or target proteins for the contrast agents are extensive. These targets can be any body compartment, cell, organ, or tissue or component thereof. The more preferred targets are those that are of diagnostic and therapeutic relevance, such as those targets associated with disease or disease states. For example, such targets can include those in body fluids, such as those in blood, plasma, lymph and fluids of the central nervous system. Further, these targets can include polypeptides or proteins that either exist in high concentration or have a large number of binding sites for certain ligands.

The targeting moieties suitable with this invention have been or will be discovered by those with ordinary skill in the art. For example, vascular blood pool imaging, serum albumin can be used as a targeting moiety. For imaging clots, fibrin can be used as target. Other protein targets include, but are not limited to, alpha acid glycoprotein, fibrinogen, fibrin, and collagen. The targeting moiety is preferably a protein or molecule that bind the target with specificity and high affinity.

It also is known that a wide range of lipophilic or amphiphilic TBMs can efficiently bind to various targets, including Human Serum Albumin (HSA). These include but are not limited to aromatic, and saturated or unsaturated aliphatic groups with 4-200 carbons wherein each carbon is optionally substituted with or replaced by oxygen, nitrogen, halogen, sulfur, or other atoms that can covalently bind carbon. For binding to other protein targets with high specificity, special targeting groups often are required. Targeting groups of sufficiently high affinity and specificity may be identified using modern techniques, such as combinatorial chemistry, high throughput screening, phage display, systemic evolution of ligands by exponential enrichment (SELEX) and other methods as described, for example, in U.S. Pat. Nos. 5,475,096, 5,595,877, and 5,270,163 (see Gold et al. Ann. Rev. of Biochem., 64: pp. 763-797 (1995)), incorporated herein by reference.

III. Linkers

The contrast agents of certain examples can include an optional linker through which the targeting moiety is attached to the scaffold protein. Preferably, the linker can be any small subunit comprising 1 to 30 carbon atoms covalently connected by single or multiple bonds wherein up to 10 of the carbon atoms may be substituted with O, N, P, S, F, and Cl. The linker functions to connect the IEMs to the scaffold. Examples of linkers include linear or branched alkanes, alkenes, or alkynes optionally substituted with functional groups such as, carbonyl, ether, amide, amine, urea, thioether, aryl, phosphate, sulfonamide and the like. The preferred linkers of certain embodiments embody two or more functional chemical groups, one of which is attached to the scaffold and the others of which are attached to the IEMs. For a short peptide fragments that is less than folded usually place at the C-terminal is preferred. F or a folded domain such as affibody, the linker can be placed the N-terminal of the protein contrast agent. Linkers can be flexible to help ensure both the contrast moiety and target moiety return their functional properties.

The preferred linkers are amino acids, especially glycine, alanine, serine, homoserine, threonine, tyrosine, cysteine, aminophenylalanine, lysine, ornithine, 2,4-diaminobutyric acid, diaminopropionic acid, hydroxyproline, aspartic acid, and glutamic acid, diols, especially ethylene glycol, dihalides, especially ethylene dichloride, 2-mercaptoethanol, 2-aminoethanol, 1,2-diaminoethanol, dicarboxylic acids, especially oxalic acid, malonic acid, malic acid, succinic acid, fumaric acid, glutaric acid, and adipic acid, and other bifunctional, trifunctional and multifunctional small molecules. Exemplary linkers include GGSGG, LGGSGGS, GGSGGS and GSG.

Still other linkers without limitation, may be urea, acetal, ketal, double ester, carbonyl, thiourea, sulfone, thioester, ester, ether, disulfide, lactone, imine, phosphoryl, or phosphodiester linkages; substituted or unsubstituted saturated or unsaturated alkyl chains; linear, branched, or cyclic amino acid chains of a single amino acid or different amino acids (e.g., extensions of the N- or C-terminus of the fibrin binding moiety); malonic, succinic, glutaric, adipic and pimelic acids; caproic acid; simple diamines and dialcohols.

Preferably the molecular weight of the linker is well defined. The molecular weights can range in size from less than 100 to greater than 1000. Preferably the molecular weight of the linker is less than 200 and even more preferably is less than 100. In addition, it may be desirable to utilize a linker that is biodegradable in vivo to provide efficient routes of excretion for the imaging agents of the present invention. Depending on their location within the linker, such biodegradable functionalities can include ester, diester, amide, phosphoester, ether, acetal, and ketal functionalities.

On of ordinary skill in the art can select a suitable linker without undue experimentation.

IV. Metal Ions

Metal ions are atoms and ions, including the respective isotopes and radioisotopes, that can bind to proteins or peptides. A metal ion may bind reversibly or irreversibly and such a bond may be covalent or non-covalent. While $Gd^{3+}$ is used in preferred embodiments of this invention as an exemplary metal ion for MRI contrast agents, it is understood that metal ions suitable with this invention include, but are not limited to metal ions including paramagnetic metal ions, transition metal ions, and Lanthanide Series ions. Exemplary metal ions include, but are not limited to, the ion, isotope, and/or radioisotope forms of magnesium, calcium, scandium, titanium, manganese, iron, boron, chromium, cobalt, nickel, cooper, zinc, gallium, strontium, yttrium, strontium, technetium, ruthenium, indium, hafnium, tungsten, rhenium, osmium, and bismuth. It is also possible to use radioisotopes of metals with this invention. Paramagnetic metal ions are the preferred metal ions for use with this invention.

The metal ions chosen to be chelated by the contrast agents depend in part on the diagnostic role of the ion. Metals that can be incorporated, e.g. through chelation, include lanthanides and other metal ions, including isotopes and radioisotopes thereof. For MR imaging applications, the preferred metal ion is paramagnetic metal ion such as gadolinium. One of ordinary skill in the art can select a metal ion for chelation, based on the intended diagnostic application, without undue experimentation.

As mentioned, the choice of metal ions to be held in chelate complexes by the contrast agents of the invention depends upon the diagnostic technique for which the agent is to be used. For MRI or MRS or EPR applications, the metal ions should be paramagnetic (metal ions with unpaired electrons), and preferably non-radioactive. For X-ray and ultrasound imaging, heavy metal ions, e.g. with atomic numbers of at least 37, preferably at least 50, should be used, again preferably non-radioactive species. For scintigraphy the metal ions should be ions of radioactive isotopes. For MR, X-ray, EIT or magnetometric imaging, one may use chelating groups to bind to heavy metal clusters (e.g. polyoxoanions and full or partial sulfur analogues) or to iron oxides or other superparamagnetic polyatomic species.

Methods of complexing metal ions with chelants and polychelants are known to those with ordinary skill in the art. Metal may be incorporated into the contrast agent, i.e. the tailored binding sites, by direct incorporation, template synthesis, and transmetallation. Preferably, the metal ion is chelated into the contrast agent by direct incorporation, which involves titration with solution of sub-stoichiometric levels up to full incorporation.

Uses and Preparations

Contrast agents prepared according to this invention can be used in the same manner as many conventional MRI and optical contrast agents. The compositions may be formulated in accordance with routine procedures as a pharmaceutical composition adapted for intravenous administration to human beings or in animal model systems.

EXAMPLES

Example 1

This example demonstrates that a contrast agent with gastrin receptor peptide (GRP) receptors binds cancer cells. An ELISA assay in three cell lines has shown that an exemplary contrast agent CD2.CA1.CD2-Bom (see below) with a targeting moiety of gastrin receptor peptide (GNQ-WAVGHLM) can be targeted to cancer cells expressing gastrin receptor peptide receptors (GRPRs). Specifically, an ELISA assay was performed on three cell lines, namely, PC-3 cell lines, SW620 cell lines, and HCT116 cell lines. Although both PC-3 cell lines and SW620 cell lines express GRPRs cells, SW620 cell lines express less GRPRs than PC-3 cell lines. HCT116 cell lines express very little GRPRs and were the control group.

The assay was conducted using cell binding analyses in that the N-terminal of the GST-fused protein was detected using an antibody against GST. The cells were cultured in wells overnight. The GST-fusion protein then was added to the culture medium. The cells were further incubated for 45 minutes. The cells then were fixed with 3.7% formaldehyde solution. The binding of the protein to the cells was analyzed by ELISA.

Figure 3:
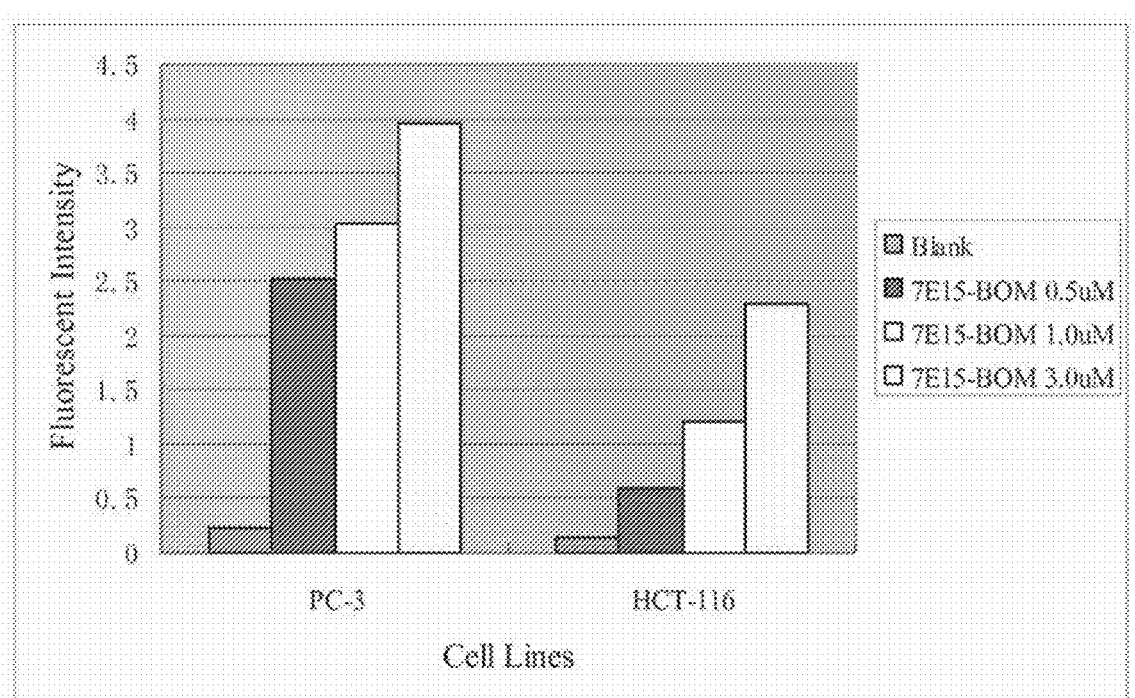
FIG. 3 shows by ELISA the binding and targeting of CA1.CD2-Bom to PC-3 cells (GRPR expression cells) and HCT-116 cells (less GRPR expression cells).

As shown in FIG. 3, the contrast agent binds preferentially to cells lines having GRPRs. It also was clear that the designed contrast agent binds PC-3 much stronger than it binds SW620, correlating with the GRPR level of the two cell lines. As expected, the binding was not observed with HCT116 cells, which lack significant levels of GRPR expression.

Example 2

This example shows that a contrast agent linked with GRP undergoes receptor mediated endocytosis. The GRPR mediated internalization of contrast protein GST-CA1.CD2-Bom was observed. The internalization of the contrast agent greatly increases the local $Gd^{3+}$ concentration. After between 45 minutes and an hour, most GST-CA1.CD2-Bom were internalized through the receptor-mediated endocytosis. The internalized GST-CA1.CD2-Bom appears to accumulate on the cytosolic side-attached to the membrane. However, it has been observed that endocytosis of GST-CA1.CD2-Bom did not occur to a significant level after 30 minutes.

As shown in FIG. 4A-4F, the contrast agent with GRP undergoes receptor mediated endocytosis. The binding of designed GST-CA1.CD2-Bom to the three cell lines was examined by immunostaining using antibody against GST. The staining was visualized by Zeiss 510 laser scanning confocal microscopy. No significant binding was observed with HCT116 cells (data not shown). Consistently, no toxic effects of $Gd^{3+}$ were observed for the testing cells as no significant cell death observed for two hours' additional incubation (data not shown).

More specifically, as shown in FIG. 4A, the contrast agent binds to the cell surface of the GRP receptor at 30 minutes with a clear membrane staining pattern with both SW620 and PC-3 cells. The majority of the proteins entered the cells after 120 minutes incubation in PC-3 cells (FIGS. 4D and 4E). Interestingly, the protein was stable after internalization at 120 minutes, indicating that the contrast withstands protein degradation by endocytosis.

Example 3

Figure 5:
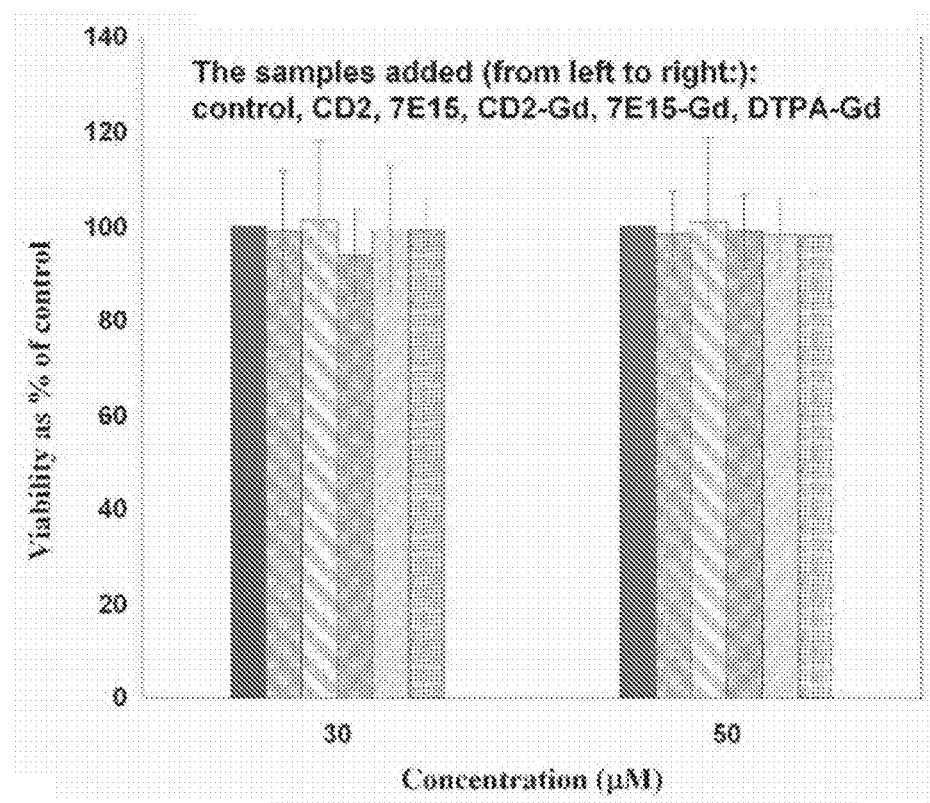
FIG. 5 shows that the contrast agents are stable and viable over time.

This example shows that the contrast agents with the targeting moiety showed no significant cytotoxicity. The cytotoxicity of designed contrast agents was examined with cell lines SW620, SW480 and HEK293 by MTT assay by an experimental procedure known in the art. Briefly, the testing cells were incubated with designed contrast agents with and without $Gd^{3+}$ (with concentration up to 50 µM) for 48 hours. The cell culture medium then was removed from the incubation. The cell viability was then analyzed by MTT assay. A slight decrease in viability was observed in HEK293 cells that were treated with w.t. CD2 and CA1.CD2 protein. No significant toxicity was observed in all tested cells treated with designed contrast agents with concentrations up to 50 µM (see FIG. 5).

The published literature suggests that GRP peptide sequences have strong affinity for the receptor with $K_d < 10^{-10}$. It is known that GRP undergoes rapid internalization after binding to its receptor GRPR. As discussed above, GST-CA1.CD2-Bom underwent internalization in PC-3 and SW620 cells. Based on these studies, it was expected that CD2-GRP (sequence) would be internalized as well. Time interval confocal and immunostaining experiments can demonstrate the timeframe for the internalization and the cellular localization after internalization of CD2-GRP. More importantly, these experiments can show the stability of CD2-GRP and the stability of the contrast agent after internalization. See FIG. 5.

Figure 6:
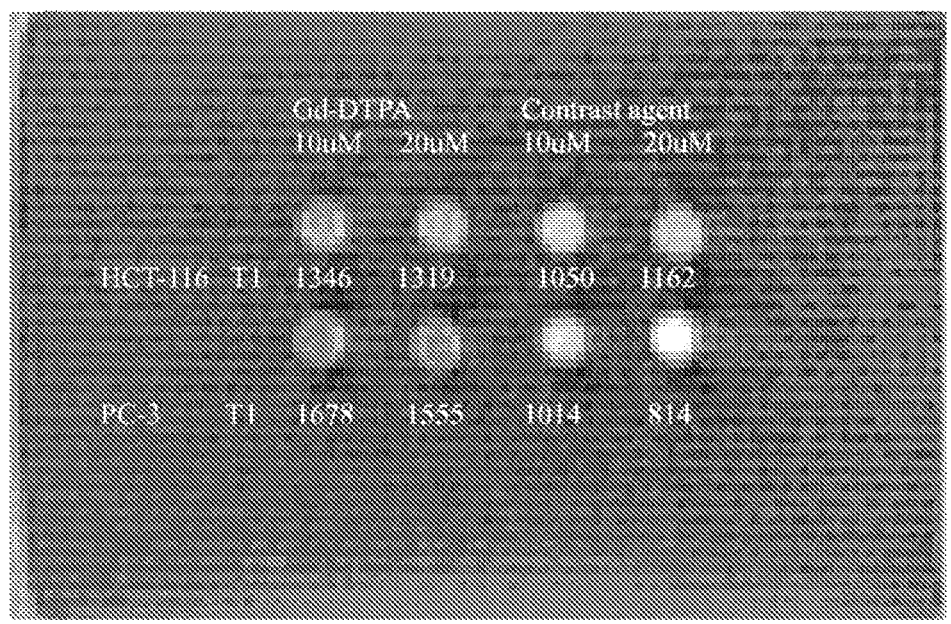
FIG. 6 shows that the MR image is enhanced by targeting of Gd-CA1.CD2-Bom to PC-3 cells and that more image enhancement is in PC-3 cells than HCT-116 cells.

If a contrast agent lacks stability or is prone to cellular degradation, the target sequence can be modified accordingly. As shown in FIG. 6, the GRP target sequence can be modified to reduce the degradation by proteases and binding affinity to the GRP receptor by blocking either N- and/or C-terminal. In addition, by grafting or engineering the targeting moiety within the stable contrast proteins will protect the proteinase degradation by carboxylases or amino-peptidases. In addition, this grafting target peptide sequences with a proper flexible linker will provide a better active conformation.

Example 4

MR Imaging of the Cells that Bind to the Designed Protein

The MR image analyses can be carried out with the same three cell lines such as PC-3, SW480, and HCT116. PC-3 cells can be grown in suspension. As the SW480 and HCT116 cells cannot be grown in suspension, these cells can be seeded in Petri dishes at a density of $4 \times 10^6$ cells per 7 ml medium. Several Petri dishes with different concentrations of the protein contrast agent can be seeded for each imaging experiment. Non-contrast protein, such as wild type CD2, can be used as a negative control and GRP peptide tagged with fluorescent probe can be used as positive controls. The cells can be pelleted after incubation at different time points. The cells can be washed three times with 5 ml PBS and collected in 200 μl PBS. The cells can be centrifuged at 800 g for 5 min, the supernatant can be removed.

Images can be obtained using imagers, such as the 3T imager (Pharmascan 300), equipped with a birdcage resonator with a 60-mm inner diameter. The sequence used to obtain the image is a spin echo with repetition time/echo time/number of excitations 100/8.45/24, field of view 3.5 cm, and one slice 1 mm.

FIG. 6 shows that the CA1.CD2-Bom provides a stronger T1 weighted cell imaging enhancement. The T1 relaxivity has been significantly shortened with CA1.CD2-Bom to PC-3 (814 ms/mM) compared to HCT-116 (1162 ms/mM) and Gd-DTPA to PC-3 (1555 ms/mM), which is consistent with the fact that PC-3 express high GRPr. The results indicate that CA1.CD2-Bom selectively enhanced the MR imaging of the cancer cells with higher GRPr expression levels.

Example 5

This examples shows exemplary contrast agents, capable of being targeted, according this invention. Examples of targeted contrast agents were created are shown in by Sequence ID Nos. 1-13.

Example 6

This example demonstrates the multifunctional probes, derived from fluorescent protein, can be directed to specific locations. FIG. 7 shows that an exemplary probe (EGFP-CA1.CD2-a-Bom10) can be directed to cells having the targeted marker (Bombesin). See, e.g., Sequence Id. Nos. 12 and 13.

Example 7

This example, in Table 1, illustrates the metal binding affinities and stabilities of 6D15 and 7E15 variants.

Table 1. Metal Binding Affinities and Stabilities of 6D15 and 7E15 Variants with Different Local Properties All $Ln^{3+}$ binding constants measured are the low limit of metal binding affinities due to the $Tb^{3+}$-FRET method used. The true binding affinities of these proteins are estimated to be significantly stronger.

Example 8

This example, in Table 2, illustrates the metal binding affinities and stabilities of 6D15 and 7E15 variants.

Table 2 Designed Metal Binding Sites in CD2

TABLE 2

| Designed metal binding sites in CD2 | |
| --- | --- |
| Designed site | Ligand residues |
| CD2-6D15 (CA4.CD2) | N15D, N17D, N60, D62 |
| CD2-7E15 (CA1.CD2) | N15E, L58E, K64D, E56, D62 |
| CD2-6D79 (CA3.CD2) | A92E, T79D, N77, E33, N90 |
| CD2-6D31 (CA2.CD2) | R31D, K43D, E29, E41 |

The foregoing detailed description of the preferred embodiments and the appended figures have been presented only for illustrative and descriptive purposes. They are not intended to be exhaustive and are not intended to limit the scope and spirit of the invention. The embodiments were selected and described to best explain the principles of the invention and its practical applications. One skilled in the art can recognize that many variations can be made to the invention disclosed in this specification without departing from the scope and spirit of the invention.

TABLE 1

Metal binding affinities and stabilities of 6D15 and 7E15 variants with different local properties

| Design Protein | 15 | 17 | 56 | 58 | 60 | 62 | 64 | Charge | $Tb^{3+}$ Kd (μM) | $La^{3+}$ Kd (μM) | $Gd^{3+}$ Kd (μM) | $Ca^{2+}$ Kd (μM) |
| --- | --- | --- | --- | --- | --- | --- | --- | --- | --- | --- | --- | --- |
| w.t CD2 | N | N | E | L | N | D | K | | | | | |
| 6D15 | D | D | | | N | D | | −3 | <8 ± 2 | <5.58 ± 2.60 | | 1400 ± 400 |
| 6D15 | A | D | | | N | D | | −2 | >1000 | | | |
| 7E15 | E | | E | D | | D | D | −5 | 0.4 ± 0.2 | <0.48 ± 0.11 | <0.04 ± 0.03 | 6 ± 3 |
| | E | | E | D | | D | E | −5 | 0.8 ± 0.2 | <0.65 ± 0.03 | | |
| | E | | E | D | | D | N | −4 | 6.3 ± 0.6 | <2.21 ± 0.41 | | 25 ± 4 |
| | E | | E | D | | D | Q | −4 | 14 ± 3 | <3.19 ± 0.67 | | 14.00 ± 0.03 |
| | E | | E | N | | D | N | −3 | 20 ± 3 | <7.66 ± 2.29 | | |
| | N | | E | N | | D | N | −2 | 42 ± 8 | <26 ± 17 | | |

All $Ln^{3+}$ binding constants measured are the low limit of metal binding affinities due to the $Tb^{3+}$-FRET method used. The true binding affinities of these proteins are estimated to be significantly stronger.

What is claimed is:

1. A recombinant protein comprising:

a domain 1 of a CD2 protein, wherein the domain 1 is modified to comprise a paramagnetic metal binding site, the paramagnetic metal binding site consisting of at least two mutations in the domain 1 of the CD2 protein, wherein the at least two mutations are selected from the group consisting of: (i) N15D and N17D; (ii) N15E, L58D, and K64E; (iii) N15E, L58D, and K64N; (iv) N15E, L58D, and, K64Q; (v) N15E, L58N, and K64N; and (vi) L58N and K64N, wherein said mutations of the domain 1 of the CD2 protein are numbered according to the amino acid sequence SEQ ID NO: 2, and wherein the recombinant protein has contrast properties.

2. The recombinant protein of claim 1, further comprising a paramagnetic ion, wherein the paramagnetic ion is Gd(III).

3. A method for preparing a contrast agent comprising: selecting a CD2 protein, wherein the CD2 protein contains at least domain 1; and modifying domain 1 of the CD2 protein to contain a paramagnetic ion binding site, the paramagnetic metal binding site consisting of at least two mutations in the domain 1 of the CD2 protein, wherein the at least two mutations are selected from the group consisting of: (i) N15D and N17D; (ii) N15E, L58D, and K64E; (iii) N15E, L58D, and K64N; (iv) N15E, L58D, and, K64Q; (v) N15E, L58N, and K64N; and (vi) L58N and K64N, wherein said mutations of the domain 1 of the CD2 protein are numbered according to the amino acid sequence SEQ ID NO: 2, to generate a modified CD2 protein wherein the recombinant protein has contrast properties.

4. The method of claim 3, further comprising the step of chelating a paramagnetic ion to the contrast agent by binding the paramagnetic ion directly at least to the N15E, L58D, and either K64E, K64N, or K64Q of the paramagnetic ion binding site.

5. The method of claim 4, wherein the paramagnetic ion is Gd(III).

6. A method of imaging a subject or a portion thereof, the method comprising: administering a recombinant protein to the subject, comprising a domain 1 of a CD2 protein, wherein the domain 1 is modified to comprise a paramagnetic metal binding site, the paramagnetic metal binding site consisting of at least two mutations in the domain 1 of the CD2 protein, wherein the at least two mutations are selected from the group consisting of: (i) N15D and N17D; (ii) N15E, L58D, and K64E; (iii) N15E, L58D, and K64N; (iv) N15E, L58D, and, K64Q; (v) N15E, L58N, and K64N; and (vi) L58N and K64N, wherein said mutations of the domain 1 of the CD2 protein are numbered according to the amino acid sequence SEQ ID NO: 2, and wherein the recombinant protein has contrast properties; and imaging the subject or the portion thereof by magnetic resonance imaging.

7. The method of claim 6, wherein the paramagnetic ion is Gd(III).

8. A recombinant protein comprising:

a domain 1 of a CD2 protein, wherein the domain 1 is modified to contain a paramagnetic metal binding site, the paramagnetic metal binding site consisting of the amino acids selected from the group consisting of (i) N15D, N17D, N60, D62, (ii) N15E, L58E, K64D, E56, D62; (iii) A92E, T79D, N77, E33, N90; and (iii) R31D, K43D, E29, E41, wherein said mutations of the domain 1 of the CD2 protein are numbered according to the amino acid sequence SEQ ID NO: 2, and wherein the recombinant protein has contrast properties.

* * * * *

SEQUENCE LISTING

<160> NUMBER OF SEQ ID NOS: 26

<210> SEQ ID NO 1
<211> LENGTH: 121
<212> TYPE: PRT
<213> ORGANISM: Artificial Sequence
<220> FEATURE:
<223> OTHER INFORMATION: Chemically synthesized sequence, derived from
      CD2, has 2 linkers (GGSGGS) flanking at Bombesin GNQWAVGHLM
      grafted at position 52.

<400> SEQUENCE: 1

Arg Asp Ser Gly Thr Val Trp Gly Ala Leu Gly His Gly Ile Glu Leu
1               5                   10                  15

Asp Ile Pro Asn Phe Gln Met Thr Asp Asp Ile Asp Glu Val Arg Trp
            20                  25                  30

Glu Arg Gly Ser Thr Leu Val Ala Glu Phe Lys Arg Lys Met Lys Pro
        35                  40                  45

Phe Leu Lys Ser Gly Gly Ser Gly Gly Ser Gly Asn Gln Trp Ala Val
    50                  55                  60

Gly His Leu Met Gly Gly Ser Gly Gly Ser Gly Ala Phe Glu Ile Asp
65                  70                  75                  80

Ala Asn Gly Asp Leu Asp Ile Lys Asn Leu Thr Arg Asp Asp Ser Gly
                85                  90                  95

Thr Tyr Asn Val Thr Val Tyr Ser Thr Asn Gly Thr Arg Ile Leu Asn
                100                 105                 110

Lys Ala Leu Asp Leu Arg Ile Leu Glu
            115                 120

<210> SEQ ID NO 2
<211> LENGTH: 114
<212> TYPE: PRT
<213> ORGANISM: Artificial Sequence
<220> FEATURE:
<223> OTHER INFORMATION: Chemically synthesized targeted contrast agent,
      derived from CD2, has a linker (GGSGG) and 10 amino acids from
      Bombesin (GNQWAVGHLM) at the terminal end.

<400> SEQUENCE: 2

Arg Asp Ser Gly Thr Val Trp Gly Ala Leu Gly His Gly Ile Glu Leu
1               5                   10                  15

Asn Ile Pro Asn Phe Gln Met Thr Asp Asp Ile Asp Glu Val Arg Trp
            20                  25                  30

Glu Arg Gly Ser Thr Leu Val Ala Glu Phe Lys Arg Lys Met Lys Pro
        35                  40                  45

Phe Leu Lys Ser Gly Ala Phe Glu Ile Asp Ala Asn Gly Asp Leu Asp
    50                  55                  60

Ile Lys Asn Leu Thr Arg Asp Asp Ser Gly Thr Tyr Asn Val Thr Val
65                  70                  75                  80

Tyr Ser Thr Asn Gly Thr Arg Ile Leu Asn Lys Ala Leu Asp Leu Arg
                85                  90                  95

Ile Leu Glu Gly Gly Ser Gly Gly Gly Asn Gln Trp Ala Val Gly His
            100                 105                 110

Leu Met

<210> SEQ ID NO 3
<211> LENGTH: 116
<212> TYPE: PRT
<213> ORGANISM: Artificial Sequence
<220> FEATURE:

<223> OTHER INFORMATION: Chemically synthesized targeted contrast agent,
derived from CD2, has a linker (LGGSGGS) and 10 amino acids from
Bombesin (GNQWAVGHLM) at the terminal end.

<400> SEQUENCE: 3

```
Arg Asp Ser Gly Thr Val Trp Gly Ala Leu Gly His Gly Ile Glu Leu
1               5                   10                  15

Asn Ile Pro Asn Phe Gln Met Thr Asp Asp Ile Asp Glu Val Arg Trp
            20                  25                  30

Glu Arg Gly Ser Thr Leu Val Ala Glu Phe Lys Arg Lys Met Lys Pro
        35                  40                  45

Phe Leu Lys Ser Gly Ala Phe Glu Ile Asp Ala Asn Gly Asp Leu Asp
    50                  55                  60

Ile Lys Asn Leu Thr Arg Asp Asp Ser Gly Thr Tyr Asn Val Thr Val
65                  70                  75                  80

Tyr Ser Thr Asn Gly Thr Arg Ile Leu Asn Lys Ala Leu Asp Leu Arg
                85                  90                  95

Ile Leu Glu Leu Gly Gly Ser Gly Gly Ser Gly Asn Gln Trp Ala Val
            100                 105                 110

Gly His Leu Met
        115
```

<210> SEQ ID NO 4
<211> LENGTH: 120
<212> TYPE: PRT
<213> ORGANISM: Artificial Sequence
<220> FEATURE:
<223> OTHER INFORMATION: Chemically synthesized targeted contrast agent,
derived from CD2, has a linker (GGSGG), 14 amino acids from
Bombesin (EQRLGNQWAVGHLM), and GG at the terminal end.

<400> SEQUENCE: 4

```
Arg Asp Ser Gly Thr Val Trp Gly Ala Leu Gly His Gly Ile Glu Leu
1               5                   10                  15

Asn Ile Pro Asn Phe Gln Met Thr Asp Asp Ile Asp Glu Val Arg Trp
            20                  25                  30

Glu Arg Gly Ser Thr Leu Val Ala Glu Phe Lys Arg Lys Met Lys Pro
        35                  40                  45

Phe Leu Lys Ser Gly Ala Phe Glu Ile Asp Ala Asn Gly Asp Leu Asp
    50                  55                  60

Ile Lys Asn Leu Thr Arg Asp Asp Ser Gly Thr Tyr Asn Val Thr Val
65                  70                  75                  80

Tyr Ser Thr Asn Gly Thr Arg Ile Leu Asn Lys Ala Leu Asp Leu Arg
                85                  90                  95

Ile Leu Glu Gly Gly Ser Gly Gly Glu Gln Arg Leu Gly Asn Gln Trp
            100                 105                 110

Ala Val Gly His Leu Met Gly Gly
        115                 120
```

<210> SEQ ID NO 5
<211> LENGTH: 116
<212> TYPE: PRT
<213> ORGANISM: Artificial Sequence
<220> FEATURE:
<223> OTHER INFORMATION: Chemically synthesized targeted contrast agent,
derived from CD2, has a linker (LGGSGGS), 10 amino acids from
Bombesin (GNQWAVGHLM), and amino acid G at the terminal end.

<400> SEQUENCE: 5

Asp Ser Gly Thr Val Trp Gly Ala Leu Gly His Gly Ile Glu Leu Asn

```
                1               5                   10                  15
Ile Pro Asn Phe Gln Met Thr Asp Asp Ile Asp Glu Val Arg Trp Glu
                20                  25                  30

Arg Gly Ser Thr Leu Val Ala Glu Phe Lys Arg Lys Met Lys Pro Phe
            35                  40                  45

Leu Lys Ser Gly Ala Phe Glu Ile Asp Ala Asn Gly Asp Leu Asp Ile
        50                  55                  60

Lys Asn Leu Thr Arg Asp Asp Ser Gly Thr Tyr Asn Val Thr Val Tyr
65                  70                  75                  80

Ser Thr Asn Gly Thr Arg Ile Leu Asn Lys Ala Leu Asp Leu Arg Ile
                85                  90                  95

Leu Glu Leu Gly Gly Ser Gly Gly Ser Gly Asn Gln Trp Ala Val Gly
                100                 105                 110

His Leu Met Gly
            115

<210> SEQ ID NO 6
<211> LENGTH: 116
<212> TYPE: PRT
<213> ORGANISM: Artificial Sequence
<220> FEATURE:
<223> OTHER INFORMATION: Chemically synthesized targeted contrast agent,
      derived from CD2, has a linker (GSG) and 14 amino acids from
      Bombesin (EQRLGNQWAVGHLM) at the terminal end.

<400> SEQUENCE: 6

Arg Asp Ser Gly Thr Val Trp Gly Ala Leu Gly His Gly Ile Glu Leu
1               5                   10                  15

Asn Ile Pro Asn Phe Gln Met Thr Asp Asp Ile Asp Glu Val Arg Trp
                20                  25                  30

Glu Arg Gly Ser Thr Leu Val Ala Glu Phe Lys Arg Lys Met Lys Pro
            35                  40                  45

Phe Leu Lys Ser Gly Ala Phe Glu Ile Asp Ala Asn Gly Asp Leu Asp
        50                  55                  60

Ile Lys Asn Leu Thr Arg Asp Asp Ser Gly Thr Tyr Asn Val Thr Val
65                  70                  75                  80

Tyr Ser Thr Asn Gly Thr Arg Ile Leu Asn Lys Ala Leu Asp Leu Arg
                85                  90                  95

Ile Leu Glu Gly Ser Gly Glu Gln Arg Leu Gly Asn Gln Trp Ala Val
                100                 105                 110

Gly His Leu Met
            115

<210> SEQ ID NO 7
<211> LENGTH: 115
<212> TYPE: PRT
<213> ORGANISM: Artificial Sequence
<220> FEATURE:
<223> OTHER INFORMATION: Chemically synthesized targeted contrast agent,
      derived from CD2, has a linker (LGGSGG), 10 amino acids from
      Bombesin (GNQWAVGHLM) at the terminal end, and two metal chelating
      sites.

<400> SEQUENCE: 7

Arg Asp Ser Gly Thr Val Trp Gly Ala Leu Gly His Gly Ile Glu Leu
1               5                   10                  15

Asp Ile Pro Asn Phe Gln Met Thr Asp Asp Ile Asp Glu Val Arg Trp
                20                  25                  30

Glu Arg Gly Ser Thr Leu Val Ala Glu Phe Lys Arg Lys Met Lys Pro
```

```
                35                  40                  45
Phe Leu Lys Ser Gly Ala Phe Glu Ile Asp Ala Asn Gly Asp Leu Asp
         50                  55                  60
Ile Lys Asn Leu Thr Arg Asp Asp Ser Gly Thr Tyr Asn Val Thr Val
 65                  70                  75                  80
Tyr Ser Thr Asn Gly Thr Arg Ile Leu Asn Lys Ala Leu Asp Leu Arg
                 85                  90                  95
Ile Leu Glu Leu Gly Gly Ser Gly Gly Gly Asn Gln Trp Ala Val Gly
                100                 105                 110
His Leu Met
        115

<210> SEQ ID NO 8
<211> LENGTH: 115
<212> TYPE: PRT
<213> ORGANISM: Artificial Sequence
<220> FEATURE:
<223> OTHER INFORMATION: Chemically synthesized targeted contrast agent,
      derived from CD2, has a linker (LGGSGG), 10 amino acids from
      Bombesin (GNQWAVGHLM) at the terminal end, and two metal chelating
      sites.

<400> SEQUENCE: 8

Arg Asp Ser Gly Thr Val Trp Gly Ala Leu Gly His Gly Ile Glu Leu
 1               5                  10                  15
Asn Ile Pro Asn Phe Gln Met Thr Asp Asp Ile Asp Glu Val Arg Trp
                20                  25                  30
Glu Arg Gly Ser Thr Leu Val Ala Glu Phe Lys Arg Lys Met Lys Pro
                35                  40                  45
Phe Leu Lys Ser Gly Ala Phe Glu Ile Asp Ala Asn Gly Asp Leu Asp
         50                  55                  60
Ile Lys Asn Leu Thr Arg Asp Asp Ser Gly Thr Tyr Asn Val Asp Val
 65                  70                  75                  80
Tyr Ser Thr Asn Gly Thr Arg Ile Leu Asn Lys Glu Leu Asp Leu Arg
                 85                  90                  95
Ile Leu Glu Leu Gly Gly Ser Gly Gly Gly Asn Gln Trp Ala Val Gly
                100                 105                 110
His Leu Met
        115

<210> SEQ ID NO 9
<211> LENGTH: 115
<212> TYPE: PRT
<213> ORGANISM: Artificial Sequence
<220> FEATURE:
<223> OTHER INFORMATION: Chemically synthesized targeted contrast agent,
      derived from CD2, has a linker (LGGSGG), 10 amino acids from
      Bombesin (GNQWAVGHLM) at the terminal end, and three metal
      chelating sites.

<400> SEQUENCE: 9

Arg Asp Ser Gly Thr Val Trp Gly Ala Leu Gly His Gly Ile Glu Leu
 1               5                  10                  15
Asp Ile Pro Asn Phe Gln Met Thr Asp Asp Ile Asp Glu Val Arg Trp
                20                  25                  30
Glu Arg Gly Ser Thr Leu Val Ala Glu Phe Lys Arg Lys Met Lys Pro
                35                  40                  45
Phe Leu Lys Ser Gly Ala Phe Glu Ile Asp Ala Asn Gly Asp Leu Asp
         50                  55                  60
```

Ile Lys Asn Leu Thr Arg Asp Asp Ser Gly Thr Tyr Asn Val Asp Val
65                  70                  75                  80

Tyr Ser Thr Asn Gly Thr Arg Ile Leu Asn Lys Glu Leu Asp Leu Arg
                85                  90                  95

Ile Leu Glu Leu Gly Gly Ser Gly Gly Asn Gln Trp Ala Val Gly
            100                 105                 110

His Leu Met
        115

<210> SEQ ID NO 10
<211> LENGTH: 219
<212> TYPE: PRT
<213> ORGANISM: Artificial Sequence
<220> FEATURE:
<223> OTHER INFORMATION: Chemically synthesized targeted contrast agent,
      derived from CD2, has two linkers (GGSGGS and GGSGG), 10 amino
      acids from Bombesin (GNQWAVGHLM) at the terminal end, two contrast
      proteins, and three metal chelating sites.

<400> SEQUENCE: 10

Arg Asp Ser Gly Thr Val Trp Gly Ala Leu Gly His Gly Ile Glu Leu
1               5                   10                  15

Asn Ile Pro Asn Phe Gln Met Thr Asp Asp Ile Asp Glu Val Arg Trp
            20                  25                  30

Glu Arg Gly Ser Thr Leu Val Ala Glu Phe Lys Arg Lys Met Lys Pro
        35                  40                  45

Phe Leu Lys Ser Gly Ala Phe Glu Ile Asp Ala Asn Gly Asp Leu Asp
    50                  55                  60

Ile Lys Asn Leu Thr Arg Asp Asp Ser Gly Thr Tyr Asn Val Thr Val
65                  70                  75                  80

Tyr Ser Thr Asn Gly Thr Arg Ile Leu Asn Lys Ala Leu Asp Leu Arg
                85                  90                  95

Ile Leu Glu Gly Gly Ser Gly Gly Ser Arg Asp Ser Gly Thr Val Trp
            100                 105                 110

Gly Ala Leu Gly His Gly Ile Glu Leu Asn Ile Pro Asn Phe Gln Met
        115                 120                 125

Thr Asp Asp Ile Asp Glu Val Arg Trp Glu Arg Gly Ser Thr Leu Val
    130                 135                 140

Ala Glu Phe Lys Arg Lys Met Lys Pro Phe Leu Lys Ser Gly Ala Phe
145                 150                 155                 160

Glu Ile Asp Ala Asn Gly Asp Leu Asp Ile Lys Asn Leu Thr Arg Asp
                165                 170                 175

Asp Ser Gly Thr Tyr Asn Val Thr Val Tyr Ser Thr Asn Gly Thr Arg
            180                 185                 190

Ile Leu Asn Lys Ala Leu Asp Leu Arg Ile Leu Glu Gly Gly Ser Gly
        195                 200                 205

Gly Gly Asn Gln Trp Ala Val Gly His Leu Met
    210                 215

<210> SEQ ID NO 11
<211> LENGTH: 148
<212> TYPE: PRT
<213> ORGANISM: Artificial Sequence
<220> FEATURE:
<223> OTHER INFORMATION: Chemically synthesized targeted contrast agent,
      derived from CD2, has a linker (LGGSGGS),10 amino acids from
      Bombesin (GNQWAVGHLM) at the terminal end, and a tag (HHHHHH) for
      Affinity purification.

<400> SEQUENCE: 11

His His His His His His Gly Met Ala Ser Met Thr Gly Gly Gln Gln
1               5                   10                  15

Met Gly Arg Asp Leu Tyr Asp Asp Asp Lys Asp Arg Trp Gly Ser
            20                  25                  30

Arg Asp Ser Gly Thr Val Trp Gly Ala Leu Gly His Gly Ile Glu Leu
            35                  40                  45

Asn Ile Pro Asn Phe Gln Met Thr Asp Asp Ile Asp Glu Val Arg Trp
50                  55                  60

Glu Arg Gly Ser Thr Leu Val Ala Glu Phe Lys Arg Lys Met Lys Pro
65                  70                  75                  80

Phe Leu Lys Ser Gly Ala Phe Glu Ile Asp Ala Asn Gly Asp Leu Asp
                85                  90                  95

Ile Lys Asn Leu Thr Arg Asp Asp Ser Gly Thr Tyr Asn Val Thr Val
            100                 105                 110

Tyr Ser Thr Asn Gly Thr Arg Ile Leu Asn Lys Ala Leu Asp Leu Arg
            115                 120                 125

Ile Leu Glu Leu Gly Gly Ser Gly Gly Ser Gly Asn Gln Trp Ala Val
            130                 135                 140

Gly His Leu Met
145

<210> SEQ ID NO 12
<211> LENGTH: 303
<212> TYPE: PRT
<213> ORGANISM: Artificial Sequence
<220> FEATURE:
<223> OTHER INFORMATION: Chemically synthesized targeted contrast agent,
      derived from GFP, has linker (GGSGG), 10 amino acids from Bombesin
      (GNQWAVGHLM) at the terminal end, and a metal binding site derived
      from the EF-hand III from calmodulin.

<400> SEQUENCE: 12

Met Ala Ser Met Thr Gly Gly Gln Gln Met Gly Arg Gly Ser Gly Pro
1               5                   10                  15

Ser Arg Met Val Ser Lys Gly Glu Glu Leu Phe Thr Gly Val Val Pro
            20                  25                  30

Ile Leu Val Glu Leu Asp Gly Asp Leu Asn Gly His Lys Phe Ser Val
            35                  40                  45

Ser Gly Glu Gly Glu Gly Asp Ala Thr Tyr Gly Lys Leu Thr Leu Lys
            50                  55                  60

Phe Ile Cys Thr Thr Gly Lys Leu Pro Val Pro Trp Pro Thr Leu Val
65                  70                  75                  80

Thr Thr Leu Thr Tyr Gly Val Gln Cys Phe Ser Arg Tyr Pro Asp His
                85                  90                  95

Met Lys Gln His Asp Phe Phe Lys Ser Ala Met Pro Glu Gly Tyr Val
            100                 105                 110

Gln Glu Arg Thr Ile Phe Phe Lys Asp Asp Gly Asn Tyr Lys Thr Arg
            115                 120                 125

Ala Glu Val Lys Phe Glu Gly Asp Thr Leu Val Asn Arg Ile Glu Leu
            130                 135                 140

Lys Gly Ile Asp Phe Lys Glu Asp Gly Asn Ile Leu Gly His Lys Leu
145                 150                 155                 160

Glu Tyr Asn Tyr Asn Ser His Asn Val Tyr Ile Met Ala Asp Lys Gln
                165                 170                 175

Glu Glu Glu Ile Arg Glu Ala Phe Arg Val Phe Asp Lys Asp Gly Asn
            180                 185                 190

```
Gly Tyr Ile Ser Ala Ala Glu Leu Arg His Val Met Thr Asn Leu Lys
            195                 200                 205

Asn Gly Ile Lys Val Asn Phe Lys Ile Arg His Asn Ile Glu Asp Gly
        210                 215                 220

Ser Val Gln Leu Ala Asp His Tyr Gln Gln Asn Thr Pro Ile Gly Asp
225                 230                 235                 240

Gly Pro Val Leu Leu Pro Asp Asn His Tyr Leu Ser Thr Gln Ser Ala
                245                 250                 255

Leu Ser Lys Asp Pro Asn Glu Lys Arg Asp His Ile Val Leu Leu Glu
            260                 265                 270

Phe Val Thr Ala Ala Gly Ile Thr Leu Gly Met Asp Glu Leu Tyr Lys
        275                 280                 285

Gly Gly Ser Gly Gly Asn Gln Trp Ala Val Gly His Leu Met
    290                 295                 300

<210> SEQ ID NO 13
<211> LENGTH: 303
<212> TYPE: PRT
<213> ORGANISM: Artificial Sequence
<220> FEATURE:
<223> OTHER INFORMATION: Chemically synthesized contrast agent, derived
      from GFP, has linker (GGSGG), 10 amino acids from Bombesin
      (GNQWAVGHLM) at the terminal end, and a metal binding site derived
      from the EF-hand III from calmodulin.

<400> SEQUENCE: 13

Met Ala Ser Met Thr Gly Gly Gln Gln Met Gly Arg Gly Ser Gly Pro
1               5                   10                  15

Ser Arg Met Val Ser Lys Gly Glu Glu Leu Phe Thr Gly Val Val Pro
            20                  25                  30

Ile Leu Val Glu Leu Asp Gly Asp Leu Asn Gly His Lys Phe Ser Val
        35                  40                  45

Ser Gly Glu Gly Glu Gly Asp Ala Thr Tyr Gly Lys Leu Thr Leu Lys
    50                  55                  60

Phe Ile Cys Thr Thr Gly Lys Leu Pro Val Pro Trp Pro Thr Leu Val
65                  70                  75                  80

Thr Thr Leu Thr Tyr Gly Val Gln Cys Phe Ser Arg Tyr Pro Asp His
                85                  90                  95

Met Lys Gln His Asp Phe Phe Lys Ser Ala Met Pro Glu Gly Tyr Val
            100                 105                 110

Gln Glu Arg Thr Ile Phe Phe Lys Asp Asp Gly Asn Tyr Lys Thr Arg
        115                 120                 125

Ala Glu Val Lys Phe Glu Gly Asp Thr Leu Val Asn Arg Ile Glu Leu
130                 135                 140

Lys Gly Ile Asp Phe Lys Glu Asp Gly Asn Ile Leu Gly His Lys Leu
145                 150                 155                 160

Glu Tyr Asn Tyr Asn Ser His Asn Val Tyr Ile Met Ala Asp Lys Gln
                165                 170                 175

Lys Asn Gly Ile Lys Val Asn Phe Lys Ile Arg His Asn Ile Glu Glu
            180                 185                 190

Glu Glu Ile Arg Glu Ala Phe Arg Val Phe Asp Lys Asp Gly Asn Gly
        195                 200                 205

Tyr Ile Ser Ala Ala Glu Leu Arg His Val Met Thr Asn Leu Asp Gly
    210                 215                 220

Ser Val Gln Leu Ala Asp His Tyr Gln Gln Asn Thr Pro Ile Gly Asp
225                 230                 235                 240
```

Gly Pro Val Leu Leu Pro Asp Asn His Tyr Leu Ser Thr Gln Ser Ala
            245                 250                 255

Leu Ser Lys Asp Pro Asn Glu Lys Arg Asp His Ile Val Leu Leu Glu
            260                 265                 270

Phe Val Thr Ala Ala Gly Ile Thr Leu Gly Met Asp Glu Leu Tyr Lys
            275                 280                 285

Gly Gly Ser Gly Gly Gly Asn Gln Trp Ala Val Gly His Leu Met
            290                 295                 300

<210> SEQ ID NO 14
<211> LENGTH: 163
<212> TYPE: PRT
<213> ORGANISM: Artificial Sequence
<220> FEATURE:
<223> OTHER INFORMATION: Chemically synthesized targeted contrast agent,
      derived from CD2, has linker (GGSGG), 59 amino acids from Affibody
      (VDNKFNKEQQNAFYEILHLPNLNEEQRNAFIQSLKDDPSQSANLLAEAKKLNDAQAPKP) at
      the terminal end, and a metal chelating site.

<400> SEQUENCE: 14

Arg Asp Ser Gly Thr Val Trp Gly Ala Leu Gly His Gly Ile Glu Leu
1               5                   10                  15

Asn Ile Pro Asn Phe Gln Met Thr Asp Asp Ile Asp Glu Val Arg Trp
            20                  25                  30

Glu Arg Gly Ser Thr Leu Val Ala Glu Phe Lys Arg Lys Met Lys Pro
        35                  40                  45

Phe Leu Lys Ser Gly Ala Phe Glu Ile Asp Ala Asn Gly Asp Leu Asp
    50                  55                  60

Ile Lys Asn Leu Thr Arg Asp Asp Ser Gly Thr Tyr Asn Val Thr Val
65                  70                  75                  80

Tyr Ser Thr Asn Gly Thr Arg Ile Leu Asn Lys Ala Leu Asp Leu Arg
                85                  90                  95

Ile Leu Glu Gly Gly Ser Gly Gly Val Asp Asn Lys Phe Asn Lys Glu
            100                 105                 110

Gln Gln Asn Ala Phe Tyr Glu Ile Leu His Leu Pro Asn Leu Asn Glu
        115                 120                 125

Glu Gln Arg Asn Ala Phe Ile Gln Ser Leu Lys Asp Asp Pro Ser Gln
    130                 135                 140

Ser Ala Asn Leu Leu Ala Glu Ala Lys Lys Leu Asn Asp Ala Gln Ala
145                 150                 155                 160

Pro Lys Pro

<210> SEQ ID NO 15
<211> LENGTH: 165
<212> TYPE: PRT
<213> ORGANISM: Artificial Sequence
<220> FEATURE:
<223> OTHER INFORMATION: Chemically synthesized targeted contrast
      agent, derived from CD2, has linker (LGGSGGS),
      59 amino acids from Affibody
      (VDNKFNKEQQNAFYEILHLPNLNEEQRNAFIQSLKDDPSQSANLLAEAKKLNDAQAPKP) at
      the terminal end, and a metal chelating site.

<400> SEQUENCE: 15

Arg Asp Ser Gly Thr Val Trp Gly Ala Leu Gly His Gly Ile Glu Leu
1               5                   10                  15

Asn Ile Pro Asn Phe Gln Met Thr Asp Asp Ile Asp Glu Val Arg Trp
            20                  25                  30

Glu Arg Gly Ser Thr Leu Val Ala Glu Phe Lys Arg Lys Met Lys Pro

```
                35                  40                  45
Phe Leu Lys Ser Gly Ala Phe Glu Ile Asp Ala Asn Gly Asp Leu Asp
         50                  55                  60
Ile Lys Asn Leu Thr Arg Asp Asp Ser Gly Thr Tyr Asn Val Thr Val
 65                  70                  75                  80
Tyr Ser Thr Asn Gly Thr Arg Ile Leu Asn Lys Ala Leu Asp Leu Arg
                 85                  90                  95
Ile Leu Glu Leu Gly Gly Ser Gly Gly Ser Val Asp Asn Lys Phe Asn
            100                 105                 110
Lys Glu Gln Gln Asn Ala Phe Tyr Glu Ile Leu His Leu Pro Asn Leu
        115                 120                 125
Asn Glu Glu Gln Arg Asn Ala Phe Ile Gln Ser Leu Lys Asp Asp Pro
    130                 135                 140
Ser Gln Ser Ala Asn Leu Leu Ala Glu Ala Lys Lys Leu Asn Asp Ala
145                 150                 155                 160

Gln Ala Pro Lys Pro
                165

<210> SEQ ID NO 16
<211> LENGTH: 113
<212> TYPE: PRT
<213> ORGANISM: Artificial Sequence
<220> FEATURE:
<223> OTHER INFORMATION: Chemically synthesized contrast agent, derived
      from CD2, has a linker (GGSGG), 9 amino acids from Somastostin
      analogue (ACYDWKVCT) at the terminal end, and a metal chelating
      site.

<400> SEQUENCE: 16

Arg Asp Ser Gly Thr Val Trp Gly Ala Leu Gly His Gly Ile Glu Leu
1               5                  10                  15
Asn Ile Pro Asn Phe Gln Met Thr Asp Asp Ile Asp Glu Val Arg Trp
            20                  25                  30
Glu Arg Gly Ser Thr Leu Val Ala Glu Phe Lys Arg Lys Met Lys Pro
        35                  40                  45
Phe Leu Lys Ser Gly Ala Phe Glu Ile Asp Ala Asn Gly Asp Leu Asp
    50                  55                  60
Ile Lys Asn Leu Thr Arg Asp Asp Ser Gly Thr Tyr Asn Val Thr Val
 65                  70                  75                  80
Tyr Ser Thr Asn Gly Thr Arg Ile Leu Asn Lys Ala Leu Asp Leu Arg
                 85                  90                  95
Ile Leu Glu Gly Gly Ser Gly Gly Ala Cys Tyr Asp Trp Lys Val Cys
            100                 105                 110
Thr

<210> SEQ ID NO 17
<211> LENGTH: 116
<212> TYPE: PRT
<213> ORGANISM: Artificial Sequence
<220> FEATURE:
<223> OTHER INFORMATION: Chemically synthesized contrast agent, derived
      from CD2, has linker (GGSGG), 12 amino acids from VIP1-12
      (HSDAVFTDNYTR) at the terminal end, a metal chelating site.

<400> SEQUENCE: 17

Arg Asp Ser Gly Thr Val Trp Gly Ala Leu Gly His Gly Ile Glu Leu
1               5                  10                  15
Asn Ile Pro Asn Phe Gln Met Thr Asp Asp Ile Asp Glu Val Arg Trp
            20                  25                  30
```

```
Glu Arg Gly Ser Thr Leu Val Ala Glu Phe Lys Arg Lys Met Lys Pro
            35                  40                  45

Phe Leu Lys Ser Gly Ala Phe Glu Ile Asp Ala Asn Gly Asp Leu Asp
        50                  55                  60

Ile Lys Asn Leu Thr Arg Asp Asp Ser Gly Thr Tyr Asn Val Thr Val
65                  70                  75                  80

Tyr Ser Thr Asn Gly Thr Arg Ile Leu Asn Lys Ala Leu Asp Leu Arg
                85                  90                  95

Ile Leu Glu Gly Gly Ser Gly Gly His Ser Asp Ala Val Phe Thr Asp
                100                 105                 110

Asn Tyr Thr Arg
            115
```

<210> SEQ ID NO 18
<211> LENGTH: 132
<212> TYPE: PRT
<213> ORGANISM: Artificial Sequence
<220> FEATURE:
<223> OTHER INFORMATION: Chemically synthesized contrast agent, derived
      from CD2, has linker (GGSGG), 28 amino acids from VIP28
      (HSDAVFTDNYTRLRKQMAVKKYLNSILN) at the terminal end, and a metal
      chelating site.

<400> SEQUENCE: 18

```
Arg Asp Ser Gly Thr Val Trp Gly Ala Leu Gly His Gly Ile Glu Leu
1               5                   10                  15

Asn Ile Pro Asn Phe Gln Met Thr Asp Asp Ile Asp Glu Val Arg Trp
                20                  25                  30

Glu Arg Gly Ser Thr Leu Val Ala Glu Phe Lys Arg Lys Met Lys Pro
            35                  40                  45

Phe Leu Lys Ser Gly Ala Phe Glu Ile Asp Ala Asn Gly Asp Leu Asp
        50                  55                  60

Ile Lys Asn Leu Thr Arg Asp Asp Ser Gly Thr Tyr Asn Val Thr Val
65                  70                  75                  80

Tyr Ser Thr Asn Gly Thr Arg Ile Leu Asn Lys Ala Leu Asp Leu Arg
                85                  90                  95

Ile Leu Glu Gly Gly Ser Gly Gly His Ser Asp Ala Val Phe Thr Asp
                100                 105                 110

Asn Tyr Thr Arg Leu Arg Lys Gln Met Ala Val Lys Lys Tyr Leu Asn
            115                 120                 125

Ser Ile Leu Asn
        130
```

<210> SEQ ID NO 19
<211> LENGTH: 134
<212> TYPE: PRT
<213> ORGANISM: Artificial Sequence
<220> FEATURE:
<223> OTHER INFORMATION: Chemically synthesized contrast agent, derived
      from CD2, has linker (GGSGG), 30 amino acids from Galanin
      (GWTLNSAGYLLGPHAVGNHRSFSDKNGLTS) at terminal end, and a metal
      chelating site.

<400> SEQUENCE: 19

```
Arg Asp Ser Gly Thr Val Trp Gly Ala Leu Gly His Gly Ile Glu Leu
1               5                   10                  15

Asn Ile Pro Asn Phe Gln Met Thr Asp Asp Ile Asp Glu Val Arg Trp
                20                  25                  30

Glu Arg Gly Ser Thr Leu Val Ala Glu Phe Lys Arg Lys Met Lys Pro
```

```
                35                  40                  45
Phe Leu Lys Ser Gly Ala Phe Glu Ile Asp Ala Asn Gly Asp Leu Asp
        50                  55                  60
Ile Lys Asn Leu Thr Arg Asp Asp Ser Gly Thr Tyr Asn Val Thr Val
65                  70                  75                  80
Tyr Ser Thr Asn Gly Thr Arg Ile Leu Asn Lys Ala Leu Asp Leu Arg
                85                  90                  95
Ile Leu Glu Gly Gly Ser Gly Gly Trp Thr Leu Asn Ser Ala Gly
                100                 105                 110
Tyr Leu Leu Gly Pro His Ala Val Gly Asn His Arg Ser Phe Ser Asp
            115                 120                 125
Lys Asn Gly Leu Thr Ser
        130
```

<210> SEQ ID NO 20
<211> LENGTH: 131
<212> TYPE: PRT
<213> ORGANISM: Artificial Sequence
<220> FEATURE:
<223> OTHER INFORMATION: Chemically synthesized contrast agent, derived
      from CD2, has linker (GGSGG), 27 amino acids from Secretin
      (HSDGTFTSELSRLREGARLQRLLQGLV) at terminal end, and a metal
      chelating site.

<400> SEQUENCE: 20

```
Arg Asp Ser Gly Thr Val Trp Gly Ala Leu Gly His Gly Ile Glu Leu
1               5                   10                  15
Asn Ile Pro Asn Phe Gln Met Thr Asp Asp Ile Asp Glu Val Arg Trp
            20                  25                  30
Glu Arg Gly Ser Thr Leu Val Ala Glu Phe Lys Arg Lys Met Lys Pro
        35                  40                  45
Phe Leu Lys Ser Gly Ala Phe Glu Ile Asp Ala Asn Gly Asp Leu Asp
        50                  55                  60
Ile Lys Asn Leu Thr Arg Asp Asp Ser Gly Thr Tyr Asn Val Thr Val
65                  70                  75                  80
Tyr Ser Thr Asn Gly Thr Arg Ile Leu Asn Lys Ala Leu Asp Leu Arg
                85                  90                  95
Ile Leu Glu Gly Gly Ser Gly Gly His Ser Asp Gly Thr Phe Thr Ser
                100                 105                 110
Glu Leu Ser Arg Leu Arg Glu Gly Ala Arg Leu Gln Arg Leu Leu Gln
            115                 120                 125
Gly Leu Val
        130
```

<210> SEQ ID NO 21
<211> LENGTH: 113
<212> TYPE: PRT
<213> ORGANISM: Artificial Sequence
<220> FEATURE:
<223> OTHER INFORMATION: Chemically synthesized contrast agent, derived
      from CD2, has linker (GGSGG), 9 amino acids from CCK8 (DYMGWMDFP)
      at the terminal end, and a metal chelating site.

<400> SEQUENCE: 21

```
Arg Asp Ser Gly Thr Val Trp Gly Ala Leu Gly His Gly Ile Glu Leu
1               5                   10                  15
Asn Ile Pro Asn Phe Gln Met Thr Asp Asp Ile Asp Glu Val Arg Trp
            20                  25                  30
Glu Arg Gly Ser Thr Leu Val Ala Glu Phe Lys Arg Lys Met Lys Pro
```

```
                35                  40                  45
Phe Leu Lys Ser Gly Ala Phe Glu Ile Asp Ala Asn Gly Asp Leu Asp
     50                  55                  60
Ile Lys Asn Leu Thr Arg Asp Asp Ser Gly Thr Tyr Asn Val Thr Val
65                  70                  75                  80
Tyr Ser Thr Asn Gly Thr Arg Ile Leu Asn Lys Ala Leu Asp Leu Arg
                 85                  90                  95
Ile Leu Glu Gly Gly Ser Gly Gly Asp Tyr Met Gly Trp Met Asp Phe
             100                 105                 110
Pro

<210> SEQ ID NO 22
<211> LENGTH: 114
<212> TYPE: PRT
<213> ORGANISM: Artificial Sequence
<220> FEATURE:
<223> OTHER INFORMATION: Chemically synthesized contrast agent, derived
      from CD2, has linker (GGSGG), 10 amino acids from human
      angiotensin I (DRVYIHPFHL) at the terminal end, and a metal
      chelating site.

<400> SEQUENCE: 22

Arg Asp Ser Gly Thr Val Trp Gly Ala Leu Gly His Gly Ile Glu Leu
1               5                   10                  15
Asn Ile Pro Asn Phe Gln Met Thr Asp Asp Ile Asp Glu Val Arg Trp
             20                  25                  30
Glu Arg Gly Ser Thr Leu Val Ala Glu Phe Lys Arg Lys Met Lys Pro
         35                  40                  45
Phe Leu Lys Ser Gly Ala Phe Glu Ile Asp Ala Asn Gly Asp Leu Asp
     50                  55                  60
Ile Lys Asn Leu Thr Arg Asp Asp Ser Gly Thr Tyr Asn Val Thr Val
65                  70                  75                  80
Tyr Ser Thr Asn Gly Thr Arg Ile Leu Asn Lys Ala Leu Asp Leu Arg
                 85                  90                  95
Ile Leu Glu Gly Gly Ser Gly Gly Asp Arg Val Tyr Ile His Pro Phe
             100                 105                 110
His Leu

<210> SEQ ID NO 23
<211> LENGTH: 125
<212> TYPE: PRT
<213> ORGANISM: Artificial Sequence
<220> FEATURE:
<223> OTHER INFORMATION: Chemically synthesized contrast agent, derived
      from CD2, has linker (GGSGG), 21 amino acids from Human Endothelin
      3 (CTCFTYKDKECVYYCHLDIIW) at the terminal end, and a metal
      chelating site.

<400> SEQUENCE: 23

Arg Asp Ser Gly Thr Val Trp Gly Ala Leu Gly His Gly Ile Glu Leu
1               5                   10                  15
Asn Ile Pro Asn Phe Gln Met Thr Asp Asp Ile Asp Glu Val Arg Trp
             20                  25                  30
Glu Arg Gly Ser Thr Leu Val Ala Glu Phe Lys Arg Lys Met Lys Pro
         35                  40                  45
Phe Leu Lys Ser Gly Ala Phe Glu Ile Asp Ala Asn Gly Asp Leu Asp
     50                  55                  60
Ile Lys Asn Leu Thr Arg Asp Asp Ser Gly Thr Tyr Asn Val Thr Val
65                  70                  75                  80
```

Tyr Ser Thr Asn Gly Thr Arg Ile Leu Asn Lys Ala Leu Asp Leu Arg
                85                  90                  95

Ile Leu Glu Gly Gly Ser Gly Gly Cys Thr Cys Phe Thr Tyr Lys Asp
            100                 105                 110

Lys Glu Cys Val Tyr Tyr Cys His Leu Asp Ile Ile Trp
        115                 120                 125

<210> SEQ ID NO 24
<211> LENGTH: 139
<212> TYPE: PRT
<213> ORGANISM: Artificial Sequence
<220> FEATURE:
<223> OTHER INFORMATION: Chemically synthesized contrast agent, derived
      from CD2, has linker (GGSGG), 35 amino acids from Human
      Neuropeptide Y (YPSKPDNPGEDAPAEDMARYYSALRHYINLITRQR) at the
      terminal end, and a metal chelating site.

<400> SEQUENCE: 24

Arg Asp Ser Gly Thr Val Trp Gly Ala Leu Gly His Gly Ile Glu Leu
1               5                   10                  15

Asn Ile Pro Asn Phe Gln Met Thr Asp Asp Ile Asp Glu Val Arg Trp
            20                  25                  30

Glu Arg Gly Ser Thr Leu Val Ala Glu Phe Lys Arg Lys Met Lys Pro
        35                  40                  45

Phe Leu Lys Ser Gly Ala Phe Glu Ile Asp Ala Asn Gly Asp Leu Asp
50                  55                  60

Ile Lys Asn Leu Thr Arg Asp Asp Ser Gly Thr Tyr Asn Val Thr Val
65                  70                  75                  80

Tyr Ser Thr Asn Gly Thr Arg Ile Leu Asn Lys Ala Leu Asp Leu Arg
                85                  90                  95

Ile Leu Glu Gly Gly Ser Gly Gly Tyr Pro Ser Lys Pro Asp Asn Pro
            100                 105                 110

Gly Glu Asp Ala Pro Ala Glu Asp Met Ala Arg Tyr Tyr Ser Ala Leu
        115                 120                 125

Arg His Tyr Ile Asn Leu Ile Thr Arg Gln Arg
    130                 135

<210> SEQ ID NO 25
<211> LENGTH: 120
<212> TYPE: PRT
<213> ORGANISM: Artificial Sequence
<220> FEATURE:
<223> OTHER INFORMATION: Chemically synthesized contrast agent, derived
      from CD2, has linker (GGSGG), 16 amino acids from Human Opioid
      peptide a-Endorphin (YGGFMTSEKSQTPLVT) at the terminal end, and a
      metal chelating site.

<400> SEQUENCE: 25

Arg Asp Ser Gly Thr Val Trp Gly Ala Leu Gly His Gly Ile Glu Leu
1               5                   10                  15

Asn Ile Pro Asn Phe Gln Met Thr Asp Asp Ile Asp Glu Val Arg Trp
            20                  25                  30

Glu Arg Gly Ser Thr Leu Val Ala Glu Phe Lys Arg Lys Met Lys Pro
        35                  40                  45

Phe Leu Lys Ser Gly Ala Phe Glu Ile Asp Ala Asn Gly Asp Leu Asp
50                  55                  60

Ile Lys Asn Leu Thr Arg Asp Asp Ser Gly Thr Tyr Asn Val Thr Val
65                  70                  75                  80

Tyr Ser Thr Asn Gly Thr Arg Ile Leu Asn Lys Ala Leu Asp Leu Arg

-continued

```
                85                  90                  95

Ile Leu Glu Gly Gly Ser Gly Gly Tyr Gly Gly Phe Met Thr Ser Glu
            100                 105                 110

Lys Ser Gln Thr Pro Leu Val Thr
        115                 120

<210> SEQ ID NO 26
<211> LENGTH: 114
<212> TYPE: PRT
<213> ORGANISM: Artificial Sequence
<220> FEATURE:
<223> OTHER INFORMATION: Chemically synthesized contrast agent, derived
      from CD2, has linker (GGSGG), 10 amino acids from GH-RH
      (EHWSYGLRPG) at the terminal end, and a metal chelating site.

<400> SEQUENCE: 26

Arg Asp Ser Gly Thr Val Trp Gly Ala Leu Gly His Gly Ile Glu Leu
1               5                   10                  15

Asn Ile Pro Asn Phe Gln Met Thr Asp Asp Ile Asp Glu Val Arg Trp
            20                  25                  30

Glu Arg Gly Ser Thr Leu Val Ala Glu Phe Lys Arg Lys Met Lys Pro
        35                  40                  45

Phe Leu Lys Ser Gly Ala Phe Glu Ile Asp Ala Asn Gly Asp Leu Asp
    50                  55                  60

Ile Lys Asn Leu Thr Arg Asp Asp Ser Gly Thr Tyr Asn Val Thr Val
65                  70                  75                  80

Tyr Ser Thr Asn Gly Thr Arg Ile Leu Asn Lys Ala Leu Asp Leu Arg
                85                  90                  95

Ile Leu Glu Gly Gly Ser Gly Gly Glu His Trp Ser Tyr Gly Leu Arg
            100                 105                 110

Pro Gly
```